United States Patent
Cohen et al.

(10) Patent No.: US 10,342,768 B2
(45) Date of Patent: Jul. 9, 2019

(54) THERAPEUTIC APPROACHES FOR TREATING PARKINSON'S DISEASE

(71) Applicant: PHARNEXT, Issy les Moulineaux (FR)

(72) Inventors: Daniel Cohen, Saint Cloud (FR); Serguei Nabirochkin, Chatenay-Malabry (FR); Ilya Chumakov, Vaux-le-Penil (FR); Rodolphe Hajj, Saint Germain en Laye (FR)

(73) Assignee: PHARNEXT, Issy les Moulineaux (FR)

( * ) Notice: Subject to any disclaimer, the term of this patent is extended or adjusted under 35 U.S.C. 154(b) by 0 days.

(21) Appl. No.: 15/506,308

(22) PCT Filed: Aug. 28, 2015

(86) PCT No.: PCT/EP2015/069783
§ 371 (c)(1),
(2) Date: Feb. 24, 2017

(87) PCT Pub. No.: WO2016/030522
PCT Pub. Date: Mar. 3, 2016

(65) Prior Publication Data
US 2017/0273919 A1 Sep. 28, 2017

Related U.S. Application Data

(63) Continuation-in-part of application No. 14/473,142, filed on Aug. 29, 2014, now Pat. No. 9,248,111.

(51) Int. Cl.
| | |
|---|---|
| *A61K 31/135* | (2006.01) |
| *A61K 31/137* | (2006.01) |
| *A61K 31/4985* | (2006.01) |
| *A61P 25/16* | (2006.01) |
| *A61K 31/138* | (2006.01) |
| *A61K 31/185* | (2006.01) |
| *A61K 31/197* | (2006.01) |
| *A61K 31/198* | (2006.01) |
| *A61K 31/44* | (2006.01) |

(52) U.S. Cl.
CPC .......... *A61K 31/137* (2013.01); *A61K 31/135* (2013.01); *A61K 31/138* (2013.01); *A61K 31/185* (2013.01); *A61K 31/197* (2013.01); *A61K 31/198* (2013.01); *A61K 31/44* (2013.01); *A61K 31/4985* (2013.01); *A61P 25/16* (2018.01); *A61K 2300/00* (2013.01)

(58) Field of Classification Search
CPC .............. A61K 2300/00; A61K 31/135; A61K 31/137; A61K 31/4985; A61P 25/16
See application file for complete search history.

(56) References Cited

U.S. PATENT DOCUMENTS

| | | |
|---|---|---|
| 5,677,344 A | 10/1997 | Greenfield et al. |
| 6,391,922 B1 | 5/2002 | Fogel |
| 8,716,269 B2 | 5/2014 | Cohen et al. |
| 8,741,886 B2 | 6/2014 | Cohen et al. |
| 8,809,302 B2 | 8/2014 | Cohen et al. |
| 8,865,769 B2 | 10/2014 | Cohen et al. |
| 9,144,558 B2 | 9/2015 | Cohen et al. |
| 9,241,933 B2 | 1/2016 | Cohen et al. |
| 9,248,111 B2 | 2/2016 | Cohen et al. |
| 9,636,316 B2 | 5/2017 | Cohen et al. |
| 2001/0004640 A1 | 6/2001 | Inada et al. |
| 2001/0023246 A1 | 9/2001 | Barritault et al. |
| 2003/0181486 A1 | 9/2003 | Bartoszyk et al. |
| 2004/0102525 A1 | 5/2004 | Kozachuk |
| 2004/0209861 A1* | 10/2004 | Benavides ........... A61K 9/4858 514/210.01 |
| 2006/0276411 A1 | 12/2006 | Simard et al. |
| 2008/0188510 A1 | 8/2008 | Yoshino |
| 2009/0069419 A1 | 3/2009 | Jandeleit et al. |
| 2009/0197958 A1 | 8/2009 | Sastry et al. |
| 2011/0230659 A1 | 9/2011 | Tsukamoto et al. |
| 2012/0088744 A1 | 4/2012 | Cohen et al. |

(Continued)

FOREIGN PATENT DOCUMENTS

| | | |
|---|---|---|
| CN | 101365451 | 2/2009 |
| EP | 1 563 846 | 8/2005 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802, 784. (Year: 1995).*

Novartis, STALEVO prescription pamphlet, Sep. 28, 2010. (Year: 2010).*

The Deep Brain Stimulation of Parkinson's Disease Study Group, "Deep-Brain Stimulatin of the Subthalamic Nucleus or the Pars Interna of the Globus Pallidus in Parkinson's Disease" N.Engl.J. Med., 2001, vol. 345,No. 13,pp. 956-963. (Year: 2001).*

Hama, A. et al. "Synergistic interaction between intrathecal gamma-aminobutyrate (GABA) receptor agonists and an N-methyl-D-aspartate (NMDA) receptor antagonist in rats with neuropathic spinal cord injury pain" *Society for Neuroscience Abstract Viewer and in Itinerary Planner*, 2010, p. 1, vol. 40.

(Continued)

*Primary Examiner* — Kendra D Carter
(74) *Attorney, Agent, or Firm* — Saliwanchik, Lloyd & Eisenschenk

(57) ABSTRACT

The present invention relates to compositions and methods for the treatment of Parkinson's disease and related disorders. More specifically, the present invention relates to novel combinatorial therapies of Parkinson's disease and related disorders targeting the alpha-synuclein aggregation network. In particular, the invention relates to compounds which, alone or in combination(s), can effectively protect neuronal cells from alpha-synuclein aggregates. The invention also relates to methods of producing a drug or a drug combination for treating Parkinson's disease and to methods of treating Parkinson's disease or a related disorder.

24 Claims, 11 Drawing Sheets

(56) References Cited

U.S. PATENT DOCUMENTS

| | | |
|---|---|---|
| 2012/0115919 A1 | 5/2012 | Mueller et al. |
| 2012/0270836 A1 | 10/2012 | Cohen et al. |
| 2013/0085122 A1 | 4/2013 | Cohen et al. |
| 2013/0090307 A1 | 4/2013 | Cohen et al. |
| 2014/0038927 A1 | 2/2014 | Cohen et al. |
| 2014/0080873 A1 | 3/2014 | Cohen et al. |
| 2014/0178463 A1 | 6/2014 | Cohen et al. |
| 2014/0235599 A1 | 8/2014 | Cohen et al. |
| 2014/0357648 A1 | 12/2014 | Cohen et al. |
| 2014/0371229 A1 | 12/2014 | Cohen et al. |
| 2014/0371277 A1 | 12/2014 | Cohen et al. |
| 2014/0378440 A1 | 12/2014 | Cohen et al. |
| 2016/0000736 A1 | 1/2016 | Cohen et al. |
| 2016/0136143 A1 | 5/2016 | Cohen et al. |
| 2016/0193163 A1 | 7/2016 | Cohen et al. |
| 2016/0206603 A1 | 7/2016 | Cohen et al. |

FOREIGN PATENT DOCUMENTS

| | | |
|---|---|---|
| EP | 1 837 034 | 9/2007 |
| WO | WO 1992/19245 | 11/1992 |
| WO | WO 01/58476 | 8/2001 |
| WO | WO 03/007993 | 1/2003 |
| WO | WO 03/080068 | 10/2003 |
| WO | WO 2007/053596 | 5/2007 |
| WO | WO 2008/006070 | 1/2008 |
| WO | WO 2008/046014 | 4/2008 |
| WO | WO 2008/143361 | 11/2008 |
| WO | WO 2009/000406 | 12/2008 |
| WO | WO 2009/133128 | 11/2009 |
| WO | WO 2009/133141 | 11/2009 |
| WO | WO 2009/133142 | 11/2009 |
| WO | WO 2010/061931 | 6/2010 |
| WO | WO 2010/064100 | 6/2010 |
| WO | WO 2010/085352 | 7/2010 |
| WO | WO 2011/054759 | 5/2011 |
| WO | WO 2012/117073 | 9/2012 |
| WO | WO 2012/117075 | 9/2012 |
| WO | WO 2012/117076 | 9/2012 |
| WO | WO 2013/127917 | 9/2013 |
| WO | WO 2013/127918 | 9/2013 |

OTHER PUBLICATIONS

Lyden, P.D. et al. "Combination therapy protects ischemic brain in rats. A glutamate antagonist plus a gamma-aminobutyric acid agonist" *Stroke*, 1994, pp. 189-196, vol. 25.

Costa, C. et al. "Coactivation of $GABA_A$ and $GABA_B$ Receptor Results in Neuroprotection During In Vitro Ischemia" *Stroke*, Jan. 15, 2004, pp. 596-600, vol. 35.

Zhou, C. et al. "Neuroprotection of $\gamma$-Aminobutyric Acid Receptor Agonists Via Enhancing Neuronal Nitric Oxide Synthase (Ser847) Phosphorylation Through Increased neuronal Nitric Oxide Synthase and PSD95 Interaction and Inhibited Protein Phosphatase Activity in Cerebral Ischemia" *Journal of Neuroscience Research*, 2008, pp. 2973-2983, vol. 86.

Louzada, P. R. et al. "Taurine prevents the neurotoxicity of β-amyloid and glutamate receptor agonists: activation of GABA receptors and possible implications for Alzheimer's disease and other neurological disorders" *The FASEB Journal*, Mar. 2004, vol. 18.

Engelhard, K. et al. "Der neuroprotektive Einfluss des Glutamat-Antagonisten Acamprosat nach experimenteller zerebraler Isch ämie" *Der Anaesthesist*, Sep. 22, 2000, pp. 816, 818, and 820, vol. 49, No. 9.

Akan, P. et al. "Pregnenolone protects the PC-12 cell line against amyloid beta peptide toxicity but its sulfate ester does not" *Chemico-Biological Interactions*, 2009, pp. 65-70, vol. 177, No. 1, XP-002613421.

Andrieu, S. et al. "Association of Alzheimer's Disease Onset With Ginkgo Biloba and Other Symptomatic Cognitive Treatments in a Population of Women Aged 75 Years and Older From the EPIDOS Study" *Journal of Gerontology: Medical Sciences*, Apr. 2003, pp. 372-377, vol. 58A, No. 4, XP-009144763.

Aplin, A. C. etal. "Vascular regression and survival are differentially regulated by MT1-MMP and TIMPs in the aortic ring model of angiogenesis" *Am. J. Physiol Cell Physiol*, Aug. 2009, pp. C471-C480, vol. 297, No. 2, XP-002613424.

Dobrek, L. et al. "Future Potential Indications for Pharmacotherapy Using Renin-Angiotensin-Aldosterone System Inhibitory Agents" *Adv. Clin. Exp. Med.*, May 2010, pp. 389-398, vol. 19, No. 3, XP-009144580.

Finsterer, J. et al. "Neurotoxocarosis" *Rev. Inst. Med. Trop. S. Paulo*, pp. 279-287, Sep.-Oct. 2007, vol. 49, No. 5, XP-002623261.

Kakinuma, Y. et al. "Donepezil, an acetylcholinesterase inhibitor against Alzheimer's dementia, promotes angiogenesis in an ischemic hindlimb model" *Journal of Molecular and Cellular Cardiology*, Apr. 2010, pp. 680-693, vol. 48, No. 4, XP-26949580.

Klein, H.E. et al. "Calcium antagonists in dementias. Assessment of the therapeutic efficacy" *Munchener Medizinische Wochenschrift*, 1995, pp. 38, 41-43, vol. 137, No. 47, XP-001525484.

Lee, S.T. et al. "Reduced circulating angiogenic cells in Alzheimer disease" *Neurology*, May 1, 2009, pp. 1858-1863, vol. 72, No. 21, XP-002610857.

Lu, Y. et al. "Neuroprotective activity and evaluation of Hsp90 inhibitors in an immortalized neuronal cell line" *Bioorganic & Medicinal Chemistry*, Feb. 2009, pp. 1709-1715, vol. 17, No. 4, XP-002613422.

Parnetti, L. et al. "Vascular Dementia Italian Sulodexide Study (VA.D.I.S.S.) Clinical and Biological Results" *Thrombosis Research*, pp. 225-233, vol. 87, No. 2.

Polizopoulou, Z. S. et al. "Evaluation of a Proposed Therapeutic Protocol in 12 Dogs with Tentative Degenerative Myelopathy" *Act Veterinaria Hungarica*, pp. 293-301, Sep. 2008, vol. 56, No. 3, XP-009142152.

Pooler, A. M. et al. "The 3-hydroxy-3-methylglutaryl co-enzyme A reductase inhibitor pravastatin enhances neurite outgrowth in hippocampal neurons" *Journal of Neurochemistry*, May 2006, pp. 716-723, vol. 97, No. 3, XP-002571001.

Roehl, A. B. et al. "Neuroprotective properties of levosimendan in an in vitro model of traumatic brain injury" *BMC Neurology*, Oct. 21, 2010, pp. 1-4, vol. 10, No. 1, XP-021074880.

Spuch, C. et al. "Induction of angiogenesis by implantation of encapsulated cells expressing vegf: A new therapy approach on Alzheimer's disease?" *Journal of Neurological Sciences*, Aug. 2009, p. 260, vol. 283, No. 1-2, Issue 1, XP-002571001.

Van Den Bussche, H. et al. "Prescription patterns and effectiveness perception of anti-dementia drugs—A comparison between General Practitioners, Neurologists and Psychiatrists" *Nervenheilkunde*, 2005, pp. 485-492, vol. 24, No. 6, XP-009144765.

Wang, B. et al. "Protective Effects of Wu-Zi-Yan-Zong-Fang on Amyloid β-induced Damage In Vivo and In Vitro" *Database Biosis [Online] Biosciences Information Service*, Aug. 2009, pp. 941-948, vol. 129, No. 8.

Yoshida, K. et al. "Eplerenone Enhances Neovascularization Induced by Endothelial Progenitor Cells in Rat Hindlimb Ischemia" *18th Scientific Meeting of the European-Society-of-Hypertension*, 22nd Scientific Meeting of the Inter, Berlin, Germany, Jun. 14-19, 2008, Poster session PJ-413, XP-009144604, abstract only.

Database Biosis [Online] Bioscience Information Service, Philadelphia, PA, Yoshihiko, K. et al. "Donepezil, an acetycholiesterase inhibitor against Alzheimer's dementia, promotes angiogenesis in an ischemic limb model of nicotinic alpha 7 k0 mice" Database Accession No. PREV200800197710, Oct. 2007, pp. 1-2, vol. 116, No. 16, Suppl. S., XP-002613420.

Database Biosis [Online] Bioscience Information Service, Philadelphia, PA, Wang, B. et al. "Protective Effects of Wu-Zi-Yan-Zong-Fang on Amyloid β-induced Damage In Vivo and In Vitro" Database Accession No. PREV200900521928, Aug. 2009, pp. 1-2, vol. 129, No. 8, Suppl. S., XP-002613420.

Berenbaum, M.C., "Synergy, additivism and antagonism in immunosuppression: A Critical Review," *Clin. exp. Immunol.*, 1977, pp. 1-18, vol. 28.

Jalbert, J.J. et al., "Dementia of the Alzheimer Type," *Epidemiologic Reviews*, 2008, pp. 15-34, vol. 30.

(56) References Cited

OTHER PUBLICATIONS

Jantzen and Robinson, *Modern Pharaceutics 3rd Edition*, published 1996, Marcel Dekker Inc., New York, NY, ed. Gilbert S. Banker et al., p. 596.

Levin, E.D. et al., "Baclofen interactions with nicotine in rats: effects on memory," *Pharmacology, Biochemistry and Behavior*, 2004, pp. 343-348, vol. 79.

Rogers, S.L. et al., "Donepezil Improves Cognition and Global Function in Alzheimer Disease," *Arch Intern Med*, 1998, pp. 1021-1031, vol. 158.

Rosse, R.B. et al., "Baclofen Treatment in a Patient With Tardive Dystonia," *J. Clin Psychiatry*, 1986, pp. 474-475, vol. 47.

Wilcock, D.M. et al., "Anti-Aβ immunotherapy in Alzheimer's disease; relevance of transgenic mouse studies to clinical trials," *J. Alzheimers Dis.*, 2008, pp. 555-569, vol. 15, No. 4.

Flannery, B. A. et al. "Baclofen for Alcohol Dependence: A Preliminary Open-Label Study" *Alcohol Clin Exp Res.*, Oct. 2004, pp. 1517-1523, vol. 28, No. 10.

Colombo, G. et al. "Role of GABA(B) receptor in alcohol dependence: reducing effect of baclofen on alcohol intake and alcohol motivational properties in rats and amelioration of alcohol withdrawal syndrome and alcohol craving in human alcoholics" *Neurotoxicity Research*, 2004, vol. 6, No. 5, pp. 403-414, abstract No. 0015545024.

Soyka, M. "Efficacy of acamprostate in the relapse prevention of alcohol dependence. Results of clinical trials and therapeutical prospects" *Nervenheilkunde*, 1995, pp. 83-86, vol. 14, No. 2, abstract No. 1995201786.

Binbay, Z. et al. "The efficacy of donepezil in two cases with alcohol induced Karsakoff's syndrome" *Klinik Psikofarmakooji Bulteni*, 2008, p. 1, vol. 18, No. 1, Accession No. 2008102413, abstract only.

Lipton, S.A. "Failures and Successes of NMDA Receptor Antagonists: Molecular Basis for the Use of Open-Channel Blockers like Memantine in the Treatment of Acute and Chronic Neurologic Insults" *NeuroRx, The Journal of American Society for Experimental NeuroTherapeutics*, Jan. 2004, pp. 101-110, vol. 1.

Sanger, D.J. et al. "Effects of NMDA receptor antagonists and sigma ligands on the acquisition of conditioned fear in mice" *Psychopharmacology*, 1991, pp. 27-34, vol. 104.

Jentsch, J.D. et al. "A low dose of the alpha$_2$ agonist clonidine ameliorates the visual attention and spatial working memory deficits produced by phencyclidine administration to rats" *Psychopharmacology*, 2004, pp. 76-83, vol. 175.

Olney, J.W. et al. "Pathological Changes Induced in Cerebrocortical Neurons by Phencyclidine and Related Drugs" *Science*, Jun. 16, 1989, pp. 1360-1362, vol. 244, No. 4910.

Davis, S.M. et al. "Selfotel in Acute Ischemic Stroke: Possible Neurotoxic Effects of an NMDA Antagonist" *Stroke*, 2000, pp. 347-354, vol. 31.

Lengyel, C. et al. "Effect of a neuroprotective drug, eliprodil on cardiac repolarisation: importance of the decreased repolarisation reserve in the development of proarrhythmic risk" *British Journal of Pharmacology*, 2004, pp. 152-158, vol. 143.

Schneider, U. et al. "Effects of Acamprosate on Memory in Healthy Young Subjects" *Journal of Studies on Alcohol*, Mar. 1999, pp. 172-175, vol. 60.

Van Der Staay, F.J. et al. "Effects of the cognition impairer MK-801 on learning and memory in mice and rats" *Behavioural Brain Research* 2011, pp. 215-229, vol. 220.

Roberts, M. et al. "NMDA Receptor Antagonists Impair Memory for Nonspatial, Socially Transmitted Food Preference" *Behavioral Neuroscience*, 2002, pp. 1059-1069, vol. 116, No. 6.

Krystal, J.H. "Subanesthetic Effects of the Noncompetitive NMDA Antagonist, Ketamine, in Humans" *Arch. Gen. Psychiatry*, Mar. 1994, pp. 199-214, vol. 51.

Subhan, Z. et al. "Psychopharmacological Effects of Vinpocetine in Normal Healthy Volunteers" *Eur. J. Clin. Pharmacol*, 1985, pp. 567-571, vol. 28.

Thal, L.J. et al. "The Safety and Lack of Efficacy of Vinpocetine in Alzheimer's Disease" *J. Am. Geriatr. Soc.*, Jun. 1989, pp. 515-520, vol. 37, No. 6.

Sandyk, R. et al. "Baclofen-Induced Memory Impairment" *Clinical Neuropharmacology*, 1985, pp. 294-295, vol. 8, No. 3.

Lee, B.Y. et al. "Chronic stimulation of GABA$_A$ receptor with muscimol reduces amyloid β protein (25-35)-induced neurotoxicity in cultured rat cortical cells" *Neuroscience Research*, 2005, pp. 347-356, vol. 52.

Marcade, M. et al. "Etazolate, a neuroprotective drug linking GABA$_A$ receptor pharmacology to amyloid precursor protein processing" *Journal of Neurochemistry*, 2008, pp. 392-404, vol. 106.

Maubach, K. "GABA$_A$ Receptor Subtype Selective Cognition Enhancers" *Current Drug Targets. CNS & Neurological Disorders*, 2003, pp. 233-239, vol. 2.

2014 Alzheimer's disease facts and figures, *Alzheimer's & Dementia*, 2014, pp. e47-e92, vol. 10.

Phrma, "Researching Alzheimer's Medicines : Setbacks and Stepping Stones" 2012, pp. 1-20.

Maria, B. "Renewed focus on dementia checked by drug challenges" *Chemistry World*, 2014, pp. 1-3.

Chumakov, I. et al. "Combining two repurposed drugs as a promising approach for Alzheimer's disease therapy" *Scientific Reports*, 2015, pp. 1-12, vol. 5.

Scart-Gres, C. et al. "OC30—First Evidence of PXT00864 Effect in the Treatment of Mild AD: Results on 30 Patients From the PLEODIAL I study" *J. Prev. Alz. Dis.*, Summary of Oral Communication at the 7th Conference Clinical Trials on Alzheimer's Disease, 2014, pp. 232-233, vol. 1.

Brasser, S. M. et al. "Alcohol Effects During Acamprosate Treatment: A Dose-Response Study in Humans" *Alcoholism: Clinical and Experimental Research*, Jul. 2004, pp. 1074-1083, vol. 28, No. 7.

Froestl, W. et al. "SGS742: the first GABA$_B$ receptor antagonist in clinical trials" *Biochemical Pharmacology*, 2004, pp. 1479-1487, vol. 68.

Izquierdo, I. et al. "Correlation between the Pharmacology and Long-Term Potentiation and the Pharmacology of Memory" *Neurobiology of Learning and Memory*, 1995, pp. 19-32, vol. 63.

Nakagawa, Y. et al. "The GABA$_B$ receptor antagonist CGP36742 attenuates the baclofen- and scopolamine-induced deficit in Morris water maze task in rats" *Brain Research*, 1997, pp. 101-106, vol. 766.

Tang, A. et al. "Effect of long term baclofen treatment on recognition memory and novelty detection" *Behavioural Brain Research*, 1996, pp. 145-152, vol. 74.

Lu, P. et al. "Silibinin prevents amyloid β peptide-induced memory impairment and oxidative stress in mice" *British journal of Pharmacology*, 2009, pp. 1270-1277, vol. 157.

Carter, M. D. et al. "The Development of New Therapeutics for Alzheimer's Disease" *Clinical Pharmacology & Therapeutics*, Jan. 1, 2010, pp. 475-486, vol. 88, No. 4.

Sawyer, G. T. "Treatment of Multiple Sclerosis with Tolbutamide" *JAMA*, Oct. 1, 1960, pp. 470-473, vol. 174, No. 5.

Yoshitake, I. et al. "First Clinical Application of the DuraHeart Centrifugal Ventricular Assist Device for a Japanese Patient" *Artificial Organs*, Sep. 1, 2009, pp. 763-766, vol. 33, No. 9.

Unger, R. H. et al. "Tolbutamide-Phenformin in Ketoacidosis-Resistant Patients" *JAMA*, Dec. 24, 1960, pp. 2132-2136, vol. 174, No. 17.

Satyanarayana, S. et al. "Pharmacodynamic and Pharmacokinetic Drug Interaction of Mexiletine with Tolbutamide in Rabbits" *Indian Journal of Pharmaceutical Education and Research*, Jan. 1, 2011, pp. 40-45, vol. 45, No. 1.

Wing, L. M. H. et al. "Cotrimoxazole as an inhibitor of oxidative drug metabolism: effects of trimethoprim and sulphamethoxazole separately and combined on tolbutamide disposition" *Br. J. Clin. Pharmac.* Nov. 1, 1985, pp. 482-485, vol. 20, No. 5.

Nistico, R. et al. "The blockade of K$^+$-ATP channels has neuroprotective effects in an in vitro model of brain ischemia" *International Review of Neurobiology*, 2007, pp. 383-395, vol. 82.

(56) References Cited

OTHER PUBLICATIONS

Zhao, W. et al. "Identification of Antihypertensive Drugs Which Inhibit Amyloid-β Protein Oligomerization" *Journal of Alzheimer's Disease*, 2009, pp. 49-57, vol. 16, No. 1.
Database WPI, Thomason Scientific, Accession No. 2007-663193, Feb. 11, 2009, XP002661053, pp. 1-10.
Egashira, N. et al. "Mexiletine Reverses Oxaliplatin-Induced Neuropathic Pain in Rats" *J Pharmacol Sci*, Jan. 1, 2010, pp. 473-476, vol. 112, No. 4.
Lee, K. H. et al. "Neuroprotective effects of mexiletine on motor evoked potentials in demyelinated rat spinal cords" *Neuroscience Research*, May 1, 2010, pp. 59-64, vol. 67, No. 1.
Ates, O. et al. "Neuroprotective effect of mexiletine in the central nervous system of diabetic rats" *Molecular and Cellular Biochemistry*, Mar. 16, 2006, pp. 125-131, vol. 286, No. 1-2.
Hewitt, K. E. et al. "The use-dependent sodium channel blocker mexiletine is neuroprotective against global ischemic injury" *Brain Research*, Apr. 20, 2001, pp. 281-287, vol. 898, No. 2.
Kaptanoglu, E. et al. "Mexiletine treatment-induced inhibition of caspase-3 activation and improvement of behavioral recovery after spinal cord injury" *J Neurosurg: Spine*, Jul. 1, 2005, pp. 53-56, vol. 3.
Nishiyama, K. et al. "Mexiletine for Painful Alcoholic Neuropathy" *Internal Medicine*, Jun. 1, 1995, pp. 577-579, vol. 34, No. 6.
Kapural, L. et al. "Intrathecal Ziconotide for Complex Regional Pain Syndrome: Seven Case Reports" *Pain Practice*, Jun. 4, 2009, pp. 296-303, vol. 9, No. 4.
Tuttolomondo, A. et al. "Neuron Protection as a Therapeutic Target in Acute Ischemic Stroke" *Current Topics in Medicinal Chemistry*, Oct. 2009, pp. 1317-1334, vol. 9, No. 14.
O'Collins, V. E. et al. "Evaluation of combination therapy in animal models of cerebral ischemia" *Journal of Cerebral Blood Flow & Metabolism*, Feb. 1, 2012, pp. 585-597, vol. 32, No. 4.
Baudelet, C. et al. "Evidence for a Neuroprotective Effect of Pyrid-3-yl-sulphonyl-urea in Photochemically Induced Focal Ischaemia in Rats: Magnetic Resonance Imaging Evaluation" *J. Pharm. Pharmacol.*, Aug. 8, 1999, pp. 967-960, vol. 51, No. 8.
Nagai, H. et al. "The effect of a novel loop diuretic, torasemide, on ischemic cerebral edema in Mongolian gerbils" *Japanese Journal of Pharmacology*, Jan. 1, 1992, p. 289P, vol. 59, No. Suppl. 1, abstract P-130.
Staub, F. et al. "Swelling of glial cells in lactacidosis and by glutamate: significance of C1⁻-transport" *Brain Research*, Apr. 30, 1993, pp. 69-74, vol. 610, No. 1.
Westermaier, T. et al. "The authors reply" *Critical Care Medicine*, Oct. 1, 2010, pp. 2084-2085, vol. 38, No. 10.
Written Opinion in International Application No. PCT/EP2012/053568, dated Sep. 10, 2012, pp. 1-13.
Lal, R. et al. "Arbaclofen Placarbil, a Novel R-Baclofen Prodrug: Improved Absorption, Distribution, Metabolism, and Elimination Properties Compared with R-Baclofen" *The Journal of Pharmacology and Experimental Therapeutics*, 2009, pp. 911-921, vol. 330, No. 3.
Hanafi, R. et al. "Baclofen ester and carbamate prodrug candidates: A simultaneous chromatographic assay, resolution optimized with DryLab" *Journal of Pharmaceutical and Biomedical Analysis*, 2011, pp. 569-576, vol. 56.
Wishart, D. S. et al. "DrugBank: a knowledge for drugs, drug actions and drug targets" *Nucleic Acids Research*, 2008, pp. D901-D906, vol. 36.
Xu, F. et al. "Discovery of a novel potent $GABA_B$ receptor agonist" *Bioorganic & Medicinal Chemistry Letters*, 2011, pp. 6582-6585, vol. 21.
Ettmayer, P. et al. "Lessons Learned from Marketed and Investigational Prodrugs" *Journal of Medicinal Chemistry*, May 6, 2004, pp. 2393-2404, vol. 47, No. 10.
Lacomblez, L. et al. "Dose-Ranging Study of Riluzole in Amyotrophic Lateral Sclerosis" *Lancet*, pp. 1425-1431, vol. 347.
Samii, A. et al. "Parkinson's Disease" *Lancet*, 2004, pp. 1783-1793, vol. 363.
Savitt, J. M. et al. "Diagnosis and treatment of Parkinson disease: molecules to medicine" *The Journal of Clinical Investigation*, Jul. 2006, pp. 1744-1754, vol. 116, No. 7.
Abbott, A. "Levodopa: the story so far" *Nature*, Aug. 26, 2010, pp. S6-S7, vol. 466.
Singer, C. A. et al. "The Mitogen-Activated Protein Kinase Pathway Mediates Estrogen Neuroprotection after Glutamate Toxicity in Primary Cortical Neurons" *The Journal of Neuroscience*, Apr. 1, 1999, pp. 2455-2463, vol. 19, No. 7.
Dauer, W. et al. "Parkinson's Disease: Mechanisms and Models" *Neuron*, Sep. 11, 2003, pp. 889-909, vol. 39.
Abbott, R. D. et al. "Frequency of bowel movements and the future risk of Parkinson's disease" *Neurology*, Aug. 2001, pp. 456-462, vol. 57.
Kuyumcu, M.E. et al. "Alzheimer's Disease Is Associated with a Low Prevalence of Hypertension" *Dementia and Geriatric Cognitive Disorders*, 2012, pp. 6-10, vol. 33.
Lieberman, A. "Shaking Up Parkinson Disease: Fighting Like a Tiger, Thinking Like a Fox: a Book for the Puzzled, the Hopeful, the Willing, and the Prepared" 2002, p. 15, Ch. 1.
Larner, A.J. "A Dictionary of Neurological Signs" 2006, pp. 1-348 (see, pp. 239-241, definition of Parkinsonism, and pp. 291-292, definition of Spasticity), $2^{nd}$ Edition.
Montastruc, J.L., et al. "Parkinson's disease and hypertension" *Neurology*, 1985, p. 1., vol. 35, No. 11. Abstract only.
"Review: could Torsemide cause Seizure disorder (Epliepsy)?", http://www.ehelthme.com/d3/torsemide/sizure+disorder, printed Dec. 31, 2015, pp. 1-5.
Marco, E. et al. "Is Botulinum Toxin Type A Effective in the Treatment of Spastic Shoulder Pain in Patients after Stroke? A Double-Blind Randomized Clinical Trial", *J Rehabil Med*, 2007, vol. 39, pp. 440-447.
Jack Jr., C. et al. "Medial Temporal Atrophy on MRI in Normal Aging and Very Mild Alzheimer's Disease", *Neurology*, 1997, vol. 49(3), pp. 786-794.
Dey, N.S. et al. "Multiparticulate Drug Delivery Systems for Controlled Release" *Tropical Journal of Pharmaceutical Research*, Sep. 2008, pp. 1067-1075, vol. 7, No. 3.
Yin, N. et al. "Synergistic and Antagonistic Drug Combinations Depend on Network Topology" *PLOS one*, Apr. 2014, pp. 1-7, vol. 9, No. 4.
Foucquier, J. et al. "Analysis of drug combinations: current methodological landscape" *Pharmacology Research & Perspectives*, 2015, pp. 1-11, vol. 3, No. 3.
Bliss, C. L. "The Toxicity of Poisons Applied Jointly" pp. 585-615, 1939, vol. 26, Issue 3.
Fisher, "Medications That Can Provoke Seizures" *Epilepsy Therapy Project*, 2009, pp. 1-6.
Campbell, W.W., "Evaluation and management of peripheral nerve injury," *Clinical Neurophysiology*, Sep. 2008, vol. 119, No. 9, pp. 1951-1965.
Faroni, A., et al., "Baclofen Modulates the Expression and Release of Neurotrophins in Schwann-Like Adipose Stem Cells," *Journal of Molecular Neuroscience*, May 31, 2012, vol. 49, No. 2, pp. 233-243.
Magnaghi, V., et al., "$GABA_B$ receptors in Schwann cells influence proliferation and myelin protein expression," *European Journal of Neuroscience*, May 2004, vol. 19, No. 10, pp. 2641-2649.
Written Opinion in International Application No. PCT/EP2014/068494, dated Oct. 22, 2014, pp. 1-8.
Mccann, H. et al. "α-Synucleinopathy phenotypes" *Parkinsonism and Related Disorders*, 2014, pp. S62-S67.
Berton, F. et al. "Acamprosate Enhances N-Methyl-D-Apartate Receptor-Mediated Neurotransmission But Inhibits Presynaptic $GABA_B$ Receptors in Nucleus Accumbens Neurons" *Alcoholism: Clinical and Experimental Research*, Feb. 1998, pp. 183-191, vol. 22, No. 1.
Reis, G. et al. "Baclofen, an agonist at peripheral $GABA_B$ receptors, induces antinociception via activation of TEA-sensitive potassium channels" *British journal of Pharmacology*, 2006, pp. 733-739, vol. 149.
Lipton, S. "Paradigm shift in neuroprotection by NMDA receptor blockade: Memantine and beyond" *Nature*, Feb. 2006, pp. 160-170, vol. 5.

(56) References Cited

OTHER PUBLICATIONS

Reilly, M. et al. "Effects of Acamprosate on Neuronal Receptors and Ion Channels Expressed in Xenopus Oocytes" *Alcoholism: Clinical and Experimental Research*, pp. 188-196, 2008, vol. 32, No. 2.

Okada, S. et al. "Two Cases of Multiple Sclerosis with Painful Tonic Seizures and Dysesthesia Ameliorated by the Administration of Mexiletine" *Japanese Journal of Medicine*, Jul.-Aug. 1991, pp. 373-375, vol. 30, No. 4.

Definition of prevent, Princeton University "About WordNet." WordNet. Princeton University. 2010. <http://wordnet.princeton.edu>, accessed Sep. 18, 2012, p. 1.

Aksenova, M. et al. "Cell Culture Models of Oxidative Stress and Injury in the Central Nervous System" *Current Neurovascular Research*, 2005, pp. 73-89, No. 2.

Davies, M. "The role of GABAA receptors in mediating the effects of alcohol in the central nervous system" *J Psychiatry Neurosci*, 2003, pp. 263-274, vol. 28, No. 4.

Chio, A. et al. "Prognostic factors in ALS: A critical review" *Amyotrophic Lateral Sclerosis*, 2009, pp. 310-323, vol. 10.

Cluskey, S. et al. "Mechanisms of neurodegeneration in amyotrophic lateral sclerosis" *Journal of Clinical Pathology: Molecular Pathology*, 2001, pp. 386-392, vol. 54.

Du, E. et al. "Preferential Neuronal Loss in Layer III of the Medial Entorhinal Cortex in Rat Models of Temporal Lobe Epilepsy" *The Journal of Neuroscience*, Oct. 1995, pp. 6301-6313, vol. 15, No. 10.

Tansey, M. et al. "Neuroinflammation in Parkinson's disease: its role in neuronal death and implications for therapeutic intervention" *Neurobiol Dis.*, Mar. 2010, pp. 510-518, vol. 37, vol. 3.

Vogt, J. et al. "Lower Motor Neuron Loss in Multiple Sclerosis and Experimental Autoimmune Encephalomyelitis" *Ann Neurol*, 2009, pp. 310-322, vol. 66.

Written Opinion in International Application No. PCT/EP2015/069783, dated Nov. 18, 2015, pp. 1-5.

\* cited by examiner

THERAPEUTIC APPROACHES FOR TREATING PARKINSON'S DISEASE

CROSS-REFERENCE TO RELATED APPLICATIONS

This application is the U.S. national stage application of International Patent Application No. PCT/EP2015/069783, filed Aug. 28, 2015, which is a continuation-in-part of U.S. Ser. No. 14/473,142, filed Aug. 29, 2014, now U.S. Pat. No. 9,248,111.

FIELD OF THE INVENTION

The present invention relates to compositions and methods for the treatment of Parkinson's disease and related disorders. More specifically, the present invention relates to novel combinatorial therapies of Parkinson's disease and related disorders.

BACKGROUND OF THE INVENTION

Parkinsonism or Parkinsonian syndromes are a group of progressive, multicentric neurodegenerative disorders whose main features are tremor at rest, rigidity, bradykinesia and postural instability. Parkinson's disease (PD) is the most common form of Parkinsonism and the second most common neurodegenerative disorder after Alzheimer's disease. In industrial countries, the prevalence of PD has been estimated at approximately 0.3% of the general population, the elderly being the most at risk (4% of the population over 80 are estimated to be affected). The mean age of onset is around 60 years, although early onset (as young as 20 year old) can occur [1].

PD is often classified as a movement disorder. Rest tremor is the most common and usually among the earliest symptoms to develop. Bradykinesia also usually appears in the early stages with difficulties performing tasks such as writing or getting dressed. Hyperkinetic movement disorders have been reported as side-effects of some treatments of Parkinson's disease. In this regard, U.S. Pat. No. 5,952,389 patent discloses the use of acamprosate for alleviating levodopa-induced hyperkinetic movement disorders. Limiting secondary effects of drugs is, however, distinct and remote from treating the disease or related symptoms. Rigidity occurs and progresses to stiffness and resistance to movement of the whole body, reducing the ability to move. In the late stages, the disease progresses to postural instability, leading to impaired balance and frequent falls. Other motor symptoms such as gait or swallowing disturbances can arise. If not treated, motor symptoms can lead to the patient being bedridden after an average of ten years [2, 3].

In later stages of the disease, PD gives rise to many non-motor symptoms which vary greatly individually. Disability is then greatly worsened by the development of autonomic and neuropsychiatric disturbances. Disorders of speech, cognition, mood, behavior, and/or thought will develop, leading eventually to dementia. Other common symptoms include sensory, sleep and emotional problems. Those disorders decrease the life expectancy of the individual affected and the mortality ratios are around twice those of people without PD [2-4].

PD is an idiopathic disease and its pathophysiology also remains poorly understood [4]. However, at least 5% of PD cases can be attributed to genetic variations. Mutations within genes such as SNCA (alpha-synuclein), PRKN (parkin), LRRK2 (leucine-rich repeat kinase 2), PINK1 (PTEN-induced putative kinase 1), DJ-1, ATP13A2 and eleven gene loci (PARK1-PARK11) have been associated with familial PD [5]. DJ-1 is suspected to be an ubiquitous redox-responsive protein thereby confirming the pivotal role of oxidative stress in PD [6], that is further evidenced by the protective role of Hypoxia Inducible Factor (HIF) in nigral dopaminergic cell protection against oxidative stress, mitochondrial dysfunction and iron homeostasis disturbance [7]. Apart from genetic factors, many environmental risk factors have been proposed to be involved in the onset of PD but none with undisputed evidence. The most frequently replicated risk factor is exposure to metals, pesticides or herbicides such as Agent Orange. On another hand, smoking and caffeine consumption seems to protect individuals from PD [1].

The pathophysiology of PD is characterized by four features [4]:

(i) A synucleinopathy characterized by the abnormal accumulation of alpha-synuclein protein into inclusions called Lewy bodies in the brain. The distribution of the Lewy bodies throughout the brain varies from one individual to another but is often directly associated with the expression and degree of the clinical symptoms.

(ii) Glutamate is the most abundant excitatory neurotransmitter in the mammalian nervous system. Under pathological conditions, its abnormal accumulation in the synaptic cleft leads to glutamate receptors overactivation that results in pathological processes and finally in neuronal cell death. This process, named excitotoxicity, is commonly observed in neuronal tissues during acute and chronic neurological disorders. It is becoming evident that excitotoxicity is involved in the pathogenesis of Parkinson's disease.

(iii) A dopaminergic activity deficiency due to the death of dopamine-generating cells in the substantia nigra, a region of the midbrain. This results in a loss of muscle movement and tone control, leading to the motor symptoms of PD.

(iv) Degeneration of NANC (non-adrenergic, non-cholinergic), serotonergic and cholinergic neurons also occurs in later stages of the disease, leading to the non-motor symptoms of PD.

As no biological test is available, diagnosis of PD is mainly based on observation of clinical symptoms and exclusion of other disorders with similar clinical features [3]. Postmortem confirmation is required for a definitive diagnosis. Neurological examination by neuroimaging can be useful to detect changes in dopaminergic neurons and to rule out other diseases. Positive therapeutic response to levodopa is another diagnosis criterion. Once the diagnosis made, the progression and severity of the disease is rated using a stages scale such as the Unified Parkinson's Disease Rating Scale.

The most widely used treatment, especially at earlier stages, is the dopamine precursor, levodopa (L-DOPA) [8]. The drug brings the lacking neurotransmitter to the dopaminergic neurons, thus decreasing motor symptoms. However, most of the drug is metabolized before to reach the blood brain barrier (BBB), causing a variety of side effects, especially gastrointestinal effects (such as anorexia, nausea or vomiting), dyskinesia and psychiatric symptoms [9]. To prevent dyskinesia phenomenon, L-DOPA is therefore usually given in combination with carbidopa or benserazide (peripheral dopa decarboxylase inhibitors) and often also with catechol-O-methyl transferase inhibitors such as entacapone. These drugs aim at preventing L-DOPA metabolism before to reach the brain, enhancing the activity of the drug [8]. Although less effective at improving motor symptoms, dopamine agonists such as pergolide, cabergoline, apomorphine or lisuride and monoamine oxidase-B inhibitors (involved in the catabolic breakdown of dopamine) such as selegiline or rasagiline are commonly used at early stages of the disease. Although less effective, they may be useful at delaying the use of levodopa and thus the onset of dyskinesia [9].

Other drugs such as anticholinergics and nicotinic acetylcholine receptor agonists may be useful but their efficacy for PD remains to be confirmed [9]. Current research also focuses on neuroprotective treatments, but none of them provided evidence of improved degeneration. They target apoptosis (omigapil, CEP-1347), glutamate receptors, adenosine A2A receptor, calcium channels (isradipine), growth factors (GDNF), alpha-synuclein and inflammation [10].

Ongoing pharmaceutical research has shown a growing interest on gene therapy and neural transplantation [10].

WO 2009/133128, WO 2009/133141, WO 2009/133142, WO 2011/054759, WO 2009/068668, WO 2009/153291 disclose potential treatments for several neurodegenerative diseases, among which, PD.

PD remains so far an incurable disease and no effective disease-modifying treatment has been discovered yet. Therefore, current treatments aim at relieving symptoms and alleviate the slow progression of the disease.

SUMMARY OF INVENTION

The present invention relates to new therapeutic methods and compositions for treating Parkinsonism. The invention stems, inter alia, from the identification of drug combinations which provide improved therapeutic effect and clinical benefit to subjects having Parkinsonism condition, particularly subjects having Parkinson's disease.

More particularly, an object of the invention relates to a composition for use in the treatment of Parkinsonism, particularly Parkinson's disease, comprising one, preferably at least two drugs selected from acamprosate, baclofen, cinacalcet, mexiletine, sulfisoxazole, torasemide and tadalafil, or a salt, prodrug, derivative of any chemical purity, or sustained-release formulation thereof.

A further object of the invention is a method for treating Parkinsonism, particularly Parkinson's disease, in a subject in need thereof, comprising administering to the subject one, preferably at least two drugs selected from acamprosate, baclofen, cinacalcet, mexiletine, sulfisoxazole, torasemide and tadalafil, or a salt, prodrug, derivative of any chemical purity, or sustained-release formulation thereof.

Preferred examples of drug combinations for use in the invention include, e.g., baclofen and acamprosate, baclofen and cinacalcet, mexiletine and cinacalcet, torasemide and baclofen, torasemide and sulfisoxazole, cinacalcet and tadalafil. In a particular embodiment, the compositions and methods further comprise levodopa. In a another particular embodiment, the compositions and methods further comprise selegiline or rasagiline. In more particular embodiment, when the compositions and methods of the invention comprise a dopamine precursor, at least one compound selected from carbidopa, benserazide, tolcapone, entacapone, selegiline or rasagiline can be further used in said composition or method.

The invention also relates to any pharmaceutical compositions per se comprising any drug combination selected from baclofen and acamprosate, baclofen and cinacalcet, mexiletine and cinacalcet, torasemide and baclofen, torasemide and sulfisoxazole, cinacalcet and tadalafil.

The compositions in the invention may further comprise one or several pharmaceutically acceptable carrier(s) or excipient(s), and they may be administered repeatedly to the subject. Preferred compositions are administered orally. Moreover, the drugs may be formulated or administered together, separately or sequentially. The invention is suitable for treating Parkinsonism in any mammalian subject, particularly in a human subject, at any stage of the disease. The invention may be used e.g., to retard the development of the disease, to reduce, delay or prevent tremor, hypokinesia (e.g., bradykinesia, akinesia, rigidity), postural instability, and/or pain, and/or to increase survival.

DETAILED DESCRIPTION OF THE INVENTION

Figure 1:
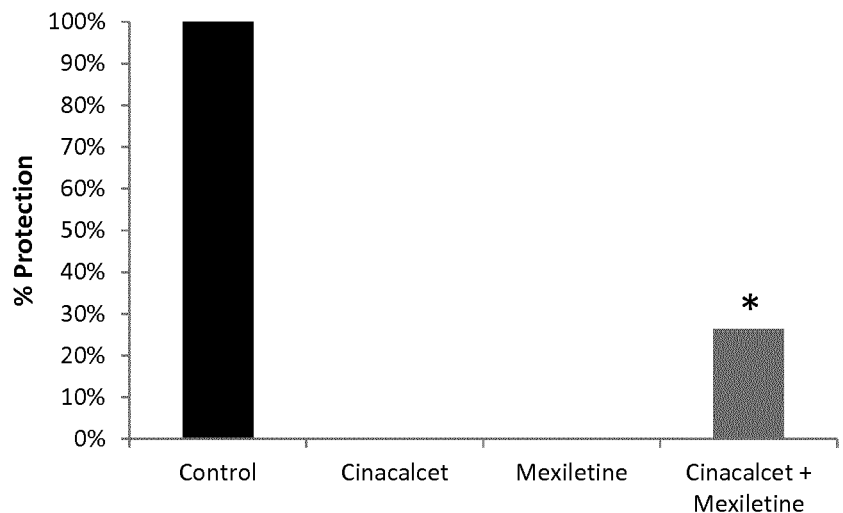
FIG. 1: Effect of cinacalcet and mexiletine combination therapy against glutamate toxicity on neuronal cortical cells. The glutamate intoxication is significantly prevented by the combination of cinacalcet (64 pM) and mexiletine (25.6 pM) whereas, at those concentrations, cinacalcet and mexiletine alone have no significant effect on intoxication. *: $p<0.001$, significantly different from glutamate intoxication; (ANOVA+Dunett's Post-Hoc test).

It is an object of the present invention to provide new therapeutic approaches for treating Parkinsonism, more specifically Parkinson's disease. More particularly the invention discloses novel use of drugs and drug combinations and methods, which allow an effective correction of such diseases and may be used in any mammalian subject.

Parkinsonism defines a group of progressive neurodegenerative disorders characterized by tremor at rest and/or bradykinesia associated with rigidity, postural instability, loss of postural reflexes, flexed posture, and/or the freezing phenomenon (when the feet are transiently "glued" to the ground). Examples of Parkinsonism conditions include Parkinson's disease, progressive supranuclear palsy, multiple system atrophy, cortical-basal ganglionic degeneration, diffuse Lewy body disease, Parkinson-dementia, X-linked dystonia-parkinsonism, and secondary Parkinsonism (resulting from environmental etiology, e.g., toxins, drugs, post encephalitic, brain tumors, head trauma, normal pressure hydrocephalus).

Parkinson's disease is the most common form of Parkinsonism. Parkinson's disease ("PD") is a neurodegenerative disorder leading to motor and non-motor manifestations and characterized by extensive degeneration of dopaminergic neurons in the nigrostriatal system. The motor manifestations of PD are attributable to the degeneration of dopaminergic neurons within the substantia nigra. They include tremor, hypokinesia (e.g., bradykinesia, akinesia, rigidity), postural instability, abnormal gait and swallowing disturbances. Non-motor symptoms include autonomic and neuropsychiatric disturbances such as anosmia, or sleep abnormalities. Within the context of the invention, the term PD includes any of the above manifestations of the disease.

As used herein, "treatment" includes the therapy, prevention, prophylaxis, retardation or reduction of symptoms provoked by or of the causes of Parkinsonism, preferably of Parkinson's disease. The term treatment also designates a retardation or delayed onset of tremor, a reduction of pain, a decrease or reduction of bradykinesia, akinesia, rigidity, postural instability, abnormal gait, anosmia, and/or sleep abnormalities, and/or an increase of survival. The term treatment includes in particular the control of disease progression and associated motor and non-motor symptoms. The term treatment particularly includes i) a protection against the toxicity caused by alpha-synuclein, or a reduction or retardation of said toxicity, and/or ii) a protection of dopaminergic neurons against the toxicity resulting from abnormal glutamate accumulation, oxidative stress, mitochondrial dysfunction or neuroinflammation, or a reduction or retardation of said toxicity, in the treated subjects.

Within the context of this invention, the designation of a specific drug or compound is meant to include not only the specifically named molecule, but also any pharmaceutically acceptable salt, hydrate, derivative, isomer, racemate, conjugate, prodrug or derivative thereof of any chemical purity.

The term "combination or combinatorial treating/therapy" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

Several biological processes such as oxidative stress, mitochondrial dysfunction and neuroinflammation accompany accumulation of aggregated alpha-synuclein which leads to the degeneration of dopaminergic neurons. On the other hand, abnormal accumulation of glutamate in synaptic cleft leads to the overactivation of glutamate receptors that results in pathological processes and finally in neuronal cell death. This process known as excitotoxicity is now recognized as an important etiological factor implicated in the development of Parkinson's disease.

The inventors were able to establish a network underlying alpha-synuclein aggregation which is a major functional network affected in Parkinson's disease. The inventors have identified functional modules composed of several target proteins, within the alpha-synuclein aggregation network. Such proteins are functionally relevant to the genesis and control of Parkinson's disease and Parkinsonism, and represent valuable targets for therapies and particularly combination therapies.

Hence, the invention relates to the use of particular drugs which, alone or preferentially in combination(s), modulate the above pathways to treat Parkinsonism, particularly Parkinson's disease.

In a particular embodiment, the present invention more specifically relates to compositions and methods using a drug combination that inhibits the activity of at least two distinct proteins involved in alpha-synuclein aggregation network. The therapeutic approaches of the invention are effective for the protection of neuronal cells, particularly for the protection of dopaminergic neurons in the midbrain and more particularly in the substantia nigra.

More particularly, the invention relates to a composition for use in the treatment of Parkinsonism, particularly Parkinson's disease (PD), comprising at least two drugs selected from acamprosate, baclofen, cinacalcet, mexiletine, sulfisoxazole, torasemide and tadalafil, or salts or prodrugs or derivatives of any purity or sustained release formulations thereof.

Indeed, the inventors have surprisingly found that these compounds show a protective activity against glutamate toxicity, which is a known cause of neuronal death in Parkinson's disease and Parkinsonism. The compounds and combination therapies of the invention also show a protective activity against ischemic stress which share common physiological features with Parkinson's disease (notably mitochondrial dysfunction and oxidative stress). More particularly compounds of the present invention are particularly efficient in vivo and in vitro against oxidative stress which is one component of alpha-synuclein toxicity for dopaminergic neurons.

The invention also relates to a method for the treatment of Parkinsonism, particularly Parkinson's disease (PD), comprising administering to a subject in need thereof at least two compounds selected from acamprosate, baclofen, cinacalcet, mexiletine, sulfisoxazole, torasemide and tadalafil, or salts or prodrugs or derivatives of any purity or sustained release formulations thereof.

The term "prodrug" as used herein refers to any functional derivatives (or precursors) of a compound of the present invention, which, when administered to a biological system (e.g. a human organism), generates said compound as a result of e.g., spontaneous chemical reaction(s), enzyme catalyzed chemical reaction(s), and/or metabolic chemical reaction(s). Prodrugs typically have the structure X-drug, wherein X is an inert carrier moiety and drug is the active compound. Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [11-15]. Furthermore, the preparation of prodrugs may be performed by conventional methods known by those skilled in the art. Methods which can be used to synthesize other prodrugs are described in numerous reviews on the subject [11, 16-22]. For example, arbaclofen placarbil is listed in ChemID plus Advance database (website: chem.sis.nlm.nih.gov/chemid-plus/) and arbaclofen placarbil is a well-known prodrug of baclofen [23, 24]. Specific examples of prodrugs of baclofen are given in Hanafi et al., 2011 [25], particularly baclofen esters and baclofen ester carbamates, which are of particular interest for CNS targeting. Hence such prodrugs are particularly suitable for compositions of this invention. Arbaclofen placarbil as mentioned before is also a well-known prodrug and may thus be used instead of baclofen in compositions of the invention. Other prodrugs of baclofen can be found in the following patent applications: WO 2010/102071, US2009197958, WO 2009/096985, WO 2009/061934, WO 2008/086492, US2009216037, WO 2005/066122, US2011021571, WO 2003/077902, and WO 2010/120370.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO 2009/033069, WO 2009/033061, WO 2009/033054 WO 2009/052191, WO 2009/033079, US20090099253, US20090069419, US20090082464, US20090082440, and US20090076147.

Prodrugs as described above can be used instead of the herein disclosed compounds of the invention.

The term "derivative" of a compound includes any molecule that is functionally and structurally related to said compound, such as an acid, amide, ester, ether, acetylated variant, hydroxylated variant, or an alkylated (C1-C6) variant of such a compound. The term "derivative" also includes structurally related compound having lost one or more substituent as listed above. For example, homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih.gov/search/) or DrugBank Worldwide Website: drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector [26, 27] available online (see Worldwide Website: ebi.ac.uk/thornton-srv/software/SMSD/). Preferred derivatives should be both structurally and functionally related to a parent compound, i.e., they should also retain at least part of the activity of the parent drug, more preferably they should have a protective activity on dopaminergic neurons from 6-OHDA-induced stress and/or glutamate toxicity and/or ischemic stress (as exemplified in the experimental part).

The term "derivative" also includes metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, preferably that has a protective activity on dopaminergic neurons from 6-OHDA-induced stress and/or glutamate toxicity and/or ischemic stress. Examples of metabolites include hydroxylated forms of torasemide resulting from the hepatic metabolism of the drug [28].

The term "salt" refers to a pharmaceutically acceptable and relatively non-toxic, inorganic or organic addition salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as taught by H. Stahl and C. G Wermuth in their handbook [29].

In a preferred embodiment, the designation of a compound is meant to designate the compound per se, as well as any pharmaceutically acceptable salt, hydrate, isomer, racemate thereof.

Table 1 below provides non limiting examples of CAS number of compounds for use in the invention as well as of salt(s), derivatives, metabolites, and/or prodrugs of these compounds.

TABLE 1

| Drug | CAS Numbers | Class or Tanimoto similarity index |
|---|---|---|
| acamprosate and related compounds | | |
| acamprosate | 77337-76-9; 77337-73-6 | NA |
| homotaurine | 3687-18-1 | 0.73 |
| Ehyl Dimethyl Ammonio Propane Sulfonate | / | 0.77 |
| taurine | 107-35-7 | 0.5 |
| baclofen and related compounds | | |
| baclofen | 1134-47-0; 66514-99-6; 69308-37-8; 70206-22-3; 63701-56-4; 63701-55-3; 28311-31-1 | NA |
| 3-(p-chlorophenyl)-4-hydroxybutyric acid | / | Metabolite |
| arbaclofen placarbil | 847353-30-4 | Prodrug |
| mexiletine and related compounds | | |
| mexiletine | 31828-71-4; 5370-01-4 | |
| 6-hydroxymethylmexiletine | 53566-98-6 | Metabolite |
| 4-hydroxymexiletine | 53566-99-7 | Metabolite |
| 3-hydroxymexiletine (MHM) | 129417-37-4 | Metabolite |
| N-hydroxymexiletine glucuronide | 151636-18-9 | Metabolite |
| sulfisoxazole and related compounds | | |
| sulfisoxazole | 127-69-5; 4299-60-9 | |
| N(4)-acetylsulfisoxazole | 4206-74-0 | Metabolite |
| sulfisoxazole acetyl | 80-74-0 | Prodrug |
| sulfamethoxazole | 723-46-6 | 0.52 |
| cinacalcet and related compounds | | |
| cinacalcet | 226256-56-0; 364782-34-3 | |
| hydrocinnamic acid | 501-52-0 | Metabolite |

TABLE 1-continued

| Drug | CAS Numbers | Class or Tanimoto similarity index |
|---|---|---|
| torasemide and related compounds | | |
| torasemide | 56211-40-6; 72810-59-4 | |
| hydroxytorasemide | 99300-68-2; 99300-67-1 | Metabolites |
| carboxytorasemide | | Metabolite |
| tolbutamide | 64-77-7 | 0.55 |
| tadalafil and related compounds | | |
| tadalafil | 171596-29-5; 171596-27-3; 171596-28-4; 629652-72-8 | |
| aminotadalafil | 385769-84-6 | 0.935 |

In a particular embodiment, a sustained-release formulation of the compound is used.

The inventors have discovered that acamprosate, baclofen, cinacalcet, mexiletine, sulfisoxazole, torasemide and tadalafil are particularly efficient in correcting alpha-synuclein aggregation molecular pathways.

As disclosed in the examples, molecules of the invention have a strong, unexpected effect on biological processes involved in Parkinsonism, particularly Parkinson's disease, and represent new therapeutic approaches of the pathology. In particular, compositions of the invention provide an unexpected protective effect against glutamate toxicity. Furthermore, drugs and drug combinations of the invention increase the dopaminergic neuron survival under 6-OHDA-induced oxidative stress as well as ischemic stress, and induce a protective effect on motor and non-motor manifestations of PD. These symptomatic improvements are to be related to the actual neuronal protection of dopaminergic neurons which results, in vivo from the treatment with the compositions of the invention. Thus, therapeutic approaches of the invention are effective for the protection of neuronal cells, particularly for the protection of dopaminergic neurons in the midbrain and more particularly in the substantia nigra as shown in vivo.

In a particular embodiment, the present invention relates to compositions and methods for treating Parkinsonism, particularly PD using a compound selected from acamprosate, baclofen, cinacalcet, mexiletine, sulfisoxazole, torasemide and tadalafil.

Drug combinations that modulate the activity of at least two distinct proteins which are involved in the alpha-synuclein aggregation network constitute a particularly advantageous embodiment of the invention. Indeed, the inventors have observed that the above drugs, when administered in combination, act synergistically to efficiently protect dopaminergic neurons. In particular, compositions of the invention have an unexpected effect on glutamate toxicity, ischemia induced cell death and oxidative stress. Such a strong and unexpected effect on biological processes involved in Parkinsonism, particularly PD, make these new combinatorial therapeutic approaches of the pathology of particular interest.

The invention thus also relates to compositions and methods for treating Parkinsonism, particularly PD, using at least two drugs selected from acamprosate, baclofen, cinacalcet, mexiletine, sulfisoxazole, torasemide and tadalafil.

The compositions and methods of the invention lead to an improvement of PD through their action on motor as well as non-motor symptoms of the disease. Therapeutic approaches of the invention provide an efficient neuronal protection, particularly of dopaminergic neurons, against oxidative stress, mitochondrial dysfunction, excitotoxicity damages, neuroinflammation or apoptosis. More particularly, they can provide a protection of the substantia nigra neurons against the toxicity of aggregated alpha-synuclein to reduce the rate or extent of dopaminergic cell loss and thereby affect the course of the disease progression.

In this regard, an object of this invention relates to a composition for use in the treatment of Parkinsonism, particularly PD, comprising a compound selected from the group consisting of acamprosate, baclofen, cinacalcet, mexiletine, sulfisoxazole, torasemide, and tadalafil or salts or prodrugs or derivatives of any purity or sustained release formulations thereof. In a preferred embodiment, the composition comprises torasemide or mexiletine, or a salt or prodrug or derivative of any purity or sustained release formulation thereof.

The invention relates to a composition for use in the treatment of Parkinsonism, particularly PD, comprising at least two compounds selected from acamprosate, baclofen, cinacalcet, mexiletine, sulfisoxazole, torasemide and tadalafil, or a salt, prodrug, derivative of any chemical purity, or sustained release formulations thereof.

The invention relates to a composition for use in the treatment of Parkinsonism, particularly PD, comprising at least one compound selected from acamprosate, cinacalcet, and torasemide, or a salt, prodrug, derivative of any chemical purity, or sustained release formulations thereof, and at least one compound selected from baclofen, mexiletine, sulfisoxazole, and tadalafil or a salt, prodrug, derivative of any chemical purity, or sustained release formulations thereof.

More particularly, the invention relates to a composition comprising at least one of the following drug combinations, for simultaneous, sequential or separate administration:
  baclofen and acamprosate,
  baclofen and cinacalcet,
  cinacalcet and acamprosate,
  mexiletine and cinacalcet,
  torasemide and baclofen,
  torasemide and sulfisoxazole, or
  cinacalcet and tadalafil,
or salt(s) or prodrug(s) or derivative(s) of any purity or sustained release formulations thereof for use in the treatment of Parkinsonism, particularly PD.

The invention also relates to methods of treating Parkinsonism, particularly PD in a subject using any one of the above drugs or compositions.

A particularly preferred composition or method of the invention uses baclofen and acamprosate, or a salt, prodrug, derivative of any chemical purity, or sustained release formulations thereof.

Another preferred composition or method of the invention uses baclofen and torasemide, or a salt, prodrug, derivative of any chemical purity, or sustained release formulations thereof.

In another particular embodiment, the composition or method of the invention uses acamprosate and cinacalcet, or salt(s) or prodrug(s) or derivative(s) of any purity or sustained release formulations, wherein the daily dosage of acamprosate is equal or lower to 10 mg.

The invention also relates to baclofen, or a salt, prodrug, derivative of any chemical purity, or sustained release formulations thereof, for use in combination with acamprosate, or a salt, prodrug, derivative of any chemical purity, or sustained release formulations thereof, for the treatment of Parkinsonism, particularly PD, by combined, separate or sequential administration to a subject.

The invention also relates to the use of any of the above composition for use in protecting a subject in need thereof from the death or degeneration of dopaminergic (DA) neurons. In a particular embodiment said subject is suffering from of Parkinsonism, and more particularly from PD.

Preferred drug compositions of the invention therefore comprise 2, 3, 4 or 5 distinct drugs, more preferably 2, 3 or 4 distinct drugs for combinatorial treatment of Parkinsonism, particularly PD in a subject in need thereof. In a preferred embodiment, the drugs of the invention are used in combination(s) for combined, separate or sequential administration, in order to provide the most effective effect.

The inventors further discovered that combination of at least one drug combination selected from the group consisting of:
- baclofen and acamprosate,
- baclofen and cinacalcet,
- mexiletine and cinacalcet,
- cinacalcet and acamprosate,
- torasemide and baclofen,
- torasemide and sulfisoxazole, or
- cinacalcet and tadalafil, with a drug, different from previous, selected from drug acamprosate, baclofen, cinacalcet, mexiletine, sulfisoxazole, torasemide, and tadalafil and which enhances the therapeutic effect of the binary combination and leads to even more efficient compositions for use in the treatment of Parkinsonism, particularly PD.

Thus, the invention also relates to a composition for use in the treatment of Parkinsonism, particularly PD, comprising cinacalcet and acamprosate in a combination with a drug selected from drug baclofen, mexiletine, sulfisoxazole, torasemide and tadalafil or salts, prodrugs, derivatives or sustained release formulations thereof, for combined, separate or sequential administration.

The invention also relates to a composition for use in the treatment of Parkinsonism, particularly PD, comprising baclofen and acamprosate in a combination with a drug selected from cinacalcet, mexiletine, sulfisoxazole, torasemide and tadalafil or salts, prodrugs, derivatives or sustained release formulations thereof, for combined, separate or sequential administration.

The invention further relates to a composition for use in the treatment of Parkinsonism, particularly PD, comprising baclofen and cinacalcet in a combination with a drug selected from acamprosate, mexiletine, sulfisoxazole, torasemide and tadalafil or salts, prodrugs, derivatives or sustained release formulations thereof, for combined, separate or sequential administration.

In an embodiment, the invention also relates to a composition for use in the treatment of Parkinsonism, particularly PD, comprising mexiletine and cinacalcet in a combination with a drug selected from acamprosate, baclofen, sulfisoxazole, torasemide and tadalafil or salts, prodrugs, derivatives or sustained release formulations thereof, for combined, separate or sequential administration.

In another embodiment, the invention relates to a composition for use in the treatment of Parkinsonism, particularly PD, comprising torasemide and baclofen in a combination with a drug selected from acamprosate, sulfisoxazole, cinacalcet, mexiletine and tadalafil or salts, prodrugs, derivatives or sustained release formulations thereof, for combined, separate or sequential administration.

In another embodiment, the invention further relates to a composition for use in the treatment of Parkinsonism, particularly PD, comprising cinacalcet and tadalafil in a combination with a drug selected from acamprosate, baclofen, mexiletine, sulfisoxazole and torasemide or salts, prodrugs, derivatives or sustained release formulations thereof, for combined, separate or sequential administration.

The invention further relates to a composition for use in the treatment of Parkinsonism, particularly PD, comprising torasemide and sulfisoxazole in a combination with a drug selected from acamprosate, baclofen, mexiletine, cinacalcet and tadalafil or salts, prodrugs, derivatives or sustained release formulations thereof, for combined, separate or sequential administration.

In a more particular embodiment, the invention relates to compositions for use in the treatment of Parkinsonism, particularly PD, comprising at least one of the following drug combinations:
- baclofen and cinacalcet and mexiletine,
- cinacalcet and acamprosate and mexiletine,
- baclofen and acamprosate and cinacalcet,
- baclofen and acamprosate and torasemide,
- baclofen and acamprosate and mexiletine,
- baclofen and acamprosate and tadalafil,
- torasemide and baclofen and cinacalcet,
- cinacalcet and tadalafil and mexiletine,
- cinacalcet and tadalafil and acamprosate, or
- cinacalcet and tadalafil and baclofen, or salts, prodrugs, derivatives or sustained release formulations thereof, for combined, separate or sequential administration.

A further object of this invention resides in the use of a composition as defined above for the manufacture of a medicament for treating Parkinsonism, particularly PD.

Another object of the invention relates to the use a composition as defined above for the manufacture of a medicament for protecting a subject in need thereof from the death or degeneration of DA neurons.

As indicated previously, in a combination therapy of this invention, the compounds or drugs may be formulated together or separately, and administered together, separately or sequentially.

A further object of the invention is a method of treating Parkinsonism, particularly PD, the method comprising simultaneously, separately or sequentially administering to a subject in need thereof an effective amount of a composition as disclosed above.

In this regard, a particular object of the invention is a method of treating Parkinsonism, particularly PD, the method comprising simultaneously, separately or sequentially administering to a subject in need thereof an effective amount of a drug combination as defined above.

In a preferred embodiment, the invention relates to a method of treating Parkinsonism, particularly PD in a subject in need thereof, comprising administering simultaneously, separately or sequentially to the subject an effective amount of a composition of at least one compound selected from the group consisting of acamprosate, baclofen, cinacalcet, mexiletine, sulfisoxazole, torasemide and tadalafil.

In a more preferred embodiment, the invention relates to a method of treating Parkinsonism, particularly PD in a subject in need thereof, comprising administering simultaneously, separately or sequentially to the subject an effective amount of a combination of at least two compounds selected from the group consisting of acamprosate, baclofen, cinacalcet, mexiletine, sulfisoxazole, torasemide and tadalafil.

In an even more preferred embodiment, the invention relates to a method of treating Parkinsonism, particularly PD in a subject in need thereof, comprising administering simultaneously, separately or sequentially to the subject an effective amount of a combination of at least one of the following drug combinations, or salts, prodrugs derivatives or sustained release formulation thereof:
baclofen and acamprosate,
baclofen and cinacalcet,
cinacalcet and acamprosate,
mexiletine and cinacalcet,
torasemide and baclofen,
torasemide and sulfisoxazole, or
cinacalcet and tadalafil.

In a another preferred embodiment, the invention relates to a method of treating Parkinsonism, particularly PD in a subject in need thereof, comprising administering simultaneously, separately or sequentially to the subject an effective amount of a combination of at least one of the following drug combinations, or salts, prodrugs derivatives or sustained release formulation thereof:
baclofen and cinacalcet and mexiletine,
cinacalcet and acamprosate and mexiletine,
baclofen and acamprosate and cinacalcet,
baclofen and acamprosate and torasemide,
baclofen and acamprosate and mexiletine,
baclofen and acamprosate and tadalafil,
torasemide and baclofen and cinacalcet,
cinacalcet and tadalafil and mexiletine,
cinacalcet and tadalafil and acamprosate, or
cinacalcet and tadalafil and baclofen.

In another embodiment, the invention relates to a method of protecting a subject in need thereof from the death or degeneration of DA neurons, said method comprising administering any of the above compositions.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds or compound combinations in an appropriate excipient or carrier.

Although very effective in vitro and in vivo, depending on the subject or specific condition, the above methods, compositions or combination therapies may further be used in conjunction or association or combination with additional drugs or treatments.

Additional therapies used in conjunction with drug(s) or drug(s) combination(s) according to the present invention, may comprise one or more drug(s) that ameliorate symptoms of PD, one or more drug(s) that could be used for palliative treatment of PD or one or more drug(s) currently evaluated in the frame of clinical trials for treating Parkinson's disease.

Therefore, compositions of the invention can be combined with dopaminergic drugs such as dopamine precursors (preferably levodopa, melevodopa), dopamine receptor agonists (preferably talipexole, piribedil, rotigotine, bromocriptine, pergolide, cabergoline, lisuride, pramipexole, ropinirole or apomorphine) or inhibitors of dopamine-metabolizing enzymes (preferably selegiline, rasagiline).

Compositions of the invention can also be combined with other known treatments for PD, adjunctive treatments for PD, or treatment of the non-motor symptoms of PD or, preferably monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine or memantine.

Such use of methods, compositions or combinations of the invention with the above mentioned therapies would permit the lowering of therapeutic doses of the concerned drugs and thus would reduce, delay or avoid known side effects associated with these drugs, for instance peak-dose dyskinesia which is observed in patients treated with levodopa.

In this regard, a further object of this invention relates to a composition for use in the treatment of Parkinsonism, particularly PD, comprising a composition as defined above, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

Hence, a particular embodiment of this invention relates to a composition for use in the treatment of Parkinsonism, particularly PD, comprising at least one compound selected from the group consisting of acamprosate, baclofen, cinacalcet, mexiletine, sulfisoxazole, torasemide, or tadalafil or salt(s), prodrug(s), derivative(s) of any chemical purity, or sustained-release formulation(s) thereof, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

A preferred embodiment of the invention relates to a composition for use in the treatment of Parkinsonism, particularly PD comprising at least one of the following drug combinations:
baclofen and levodopa,
torasemide and levodopa,
sulfisoxazole and levodopa,
mexiletine and levodopa,
cinacalcet and levodopa,
tadalafil and levodopa,
baclofen and selegiline or rasagiline,
torasemide and selegiline or rasagiline,
sulfisoxazole and selegiline or rasagiline,
mexiletine and selegiline or rasagiline,
cinacalcet and selegiline or rasagiline, or
tadalafil and selegiline or rasagiline,
or salts or prodrugs or derivatives of any purity or sustained release formulations thereof, for combined, separate or sequential administration.

The invention also relates to a composition per se comprising at least one of the following drug combinations:
baclofen and levodopa,
torasemide and levodopa,
sulfisoxazole and levodopa, mexiletine and levodopa,
cinacalcet and levodopa,
tadalafil and levodopa,
baclofen and selegiline or rasagiline,
torasemide and selegiline or rasagiline,
sulfisoxazole and selegiline or rasagiline,
mexiletine and selegiline or rasagiline,
cinacalcet and selegiline or rasagiline, or
tadalafil and selegiline or rasagiline or salts or prodrugs or derivatives of any purity or sustained release formulations thereof, for combined, separate or sequential administration.

In an embodiment, the invention relates also to a method of treating Parkinsonism, particularly PD in a subject in need thereof, comprising administering simultaneously, separately or sequentially to the subject an effective amount of a combination of at least two compounds selected from the group consisting of acamprosate, baclofen, cinacalcet, mexiletine, sulfisoxazole, torasemide or tadalafil, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another embodiment, the invention relates to a method of treating Parkinsonism, particularly PD in a subject in need thereof, comprising administering simultaneously, separately or sequentially to the subject an effective amount of baclofen and acamprosate or salts, prodrugs, derivatives or sustained release formulations thereof, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another embodiment, the invention relates to a method of treating Parkinsonism, particularly PD in a subject in need thereof, comprising administering simultaneously, separately or sequentially to the subject an effective amount of mexiletine and cinacalcet or salts, prodrugs, derivatives or sustained release formulations thereof, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another embodiment, the invention relates to a method of treating Parkinsonism, particularly PD in a subject in need thereof, comprising administering simultaneously, separately or sequentially to the subject an effective amount of torasemide and baclofen or salts, prodrugs, derivatives or sustained release formulations thereof, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another embodiment, the invention relates to a method of treating Parkinsonism, particularly PD in a subject in need thereof, comprising administering simultaneously, separately or sequentially to the subject an effective amount of sulfisoxazole and torasemide or salts, prodrugs, derivatives or sustained release formulations thereof, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another embodiment, the invention relates to a method of treating Parkinsonism, particularly PD in a subject in need thereof, comprising administering simultaneously, separately or sequentially to the subject an effective amount of cinacalcet and acamprosate or salts, prodrugs, derivatives or sustained release formulations thereof, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another embodiment, the invention relates to a method of treating Parkinsonism, particularly PD in a subject in need thereof, comprising administering simultaneously, separately or sequentially to the subject an effective amount of baclofen and cinacalcet or salts, prodrugs, derivatives or sustained release formulations thereof, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In another embodiment, the invention relates to a method of treating Parkinsonism, particularly PD in a subject in need thereof, comprising administering simultaneously, separately or sequentially to the subject an effective amount of cinacalcet and tadalafil or salts, prodrugs, derivatives or sustained release formulations thereof, in combination with at least one compound selected from the group consisting of levodopa, melevodopa, talipexole, piribedil, rotigotine, bromocriptine, pergolide, cabergoline, lisuride, pramipexole, ropinirole, apomorphine, selegiline, rasagiline, monosialotetrahexosylganglioside, citicoline, droxidopa mazaticol, promethazine, quetiapine, procyclidine, orphenadrine, domperidone, benzatropine, trihexyphenidyl, biperiden, clozapine, desipramine, citalopram, nortriptyline, paroxetine, atomoxetine, venlafaxine, amantadine, donepezil, rivastigmine and memantine, or salts or prodrugs or derivatives of any purity or sustained release formulations thereof.

In a preferred embodiment, the compositions of this invention, for use in the treatment of Parkinsonism, particularly PD, comprise at least one of the following drug combinations, or salts, prodrugs, derivatives or sustained release formulations thereof, the drugs in each of said combinations being for combined, separate or sequential administration:
  baclofen and acamprosate and levodopa,
  mexiletine and cinacalcet and levodopa,
  torasemide and baclofen and levodopa,
  baclofen and cinacalcet and levodopa,
  cinacalcet and acamprosate and levodopa,
  sulfisoxazole and torasemide and levodopa,
  cinacalcet and tadalafil and levodopa,
  baclofen and acamprosate and selegiline or rasagiline,
  mexiletine and cinacalcet and selegiline or rasagiline,
  torasemide and baclofen and selegiline or rasagiline,
  baclofen and cinacalcet and selegiline or rasagiline,
  cinacalcet and acamprosate and selegiline or rasagiline,
  sulfisoxazole and torasemide and selegiline or rasagiline, or
  cinacalcet and tadalafil and selegiline or rasagiline.

The invention also relates to a composition per se comprising at least one of the following drug combinations, or salts, prodrugs, derivatives or sustained release formulations thereof, the drugs in each of said combinations being for simultaneous, separate or sequential administration:
  baclofen and acamprosate and levodopa,
  mexiletine and cinacalcet and levodopa,
  torasemide and baclofen and levodopa,
  baclofen and cinacalcet and levodopa,
  cinacalcet and acamprosate and levodopa,
  sulfisoxazole and torasemide and levodopa,
  cinacalcet and tadalafil and levodopa,
  baclofen and acamprosate and selegiline or rasagiline,
  mexiletine and cinacalcet and selegiline or rasagiline,
  torasemide and baclofen and selegiline or rasagiline,
  baclofen and cinacalcet and selegiline or rasagiline,
  cinacalcet and acamprosate and selegiline or rasagiline,
  sulfisoxazole and torasemide and selegiline or rasagiline, or
  cinacalcet and tadalafil and selegiline or rasagiline.

In another preferred embodiment, the invention relates to compositions of this invention, for use in the treatment of Parkinsonism, particularly PD, comprise at least one of the following drug combinations, or salts, prodrugs, derivatives or sustained release formulations thereof, the drugs in each of said combinations being for combined, separate or sequential administration:
  baclofen, cinacalcet, mexiletine and levodopa,
  cinacalcet, acamprosate, mexiletine and levodopa,
  baclofen, acamprosate, cinacalcet and levodopa,
  baclofen, acamprosate, torasemide and levodopa,
  baclofen, acamprosate, mexiletine, and levodopa,
  baclofen, acamprosate, tadalafil, and levodopa,
  torasemide, baclofen, cinacalcet and levodopa,
  cinacalcet, tadalafil, mexiletine, and levodopa,
  cinacalcet, tadalafil, acamprosate, and levodopa,
  cinacalcet, tadalafil, baclofen, and levodopa
  baclofen, cinacalcet, mexiletine and selegiline or rasagiline,
  cinacalcet, acamprosate, mexiletine and selegiline or rasagiline,
  baclofen, acamprosate, cinacalcet and selegiline or rasagiline,
  baclofen, acamprosate, torasemide and selegiline or rasagiline,
  baclofen, acamprosate, mexiletine, and selegiline or rasagiline,
  baclofen, acamprosate, tadalafil, and selegiline or rasagiline,
  torasemide, baclofen, cinacalcet and selegiline or rasagiline,
  cinacalcet, tadalafil, mexiletine, and selegiline or rasagiline,
  cinacalcet, tadalafil, acamprosate, and selegiline or rasagiline, or
  cinacalcet, tadalafil, baclofen, and selegiline or rasagiline.

In a particular embodiment, when compositions or combination therapies of the invention comprise dopamine precursor, they can be further combined with at least one compound selected from peripheral dopa decarboxylase inhibitors, catechol-O-methyl transferase inhibitors or monoamine oxidase inhibitors. More particularly, when compositions or combination therapies of the invention comprise a dopamine precursor, they can be further combined with at least one compound selected from carbidopa, benserazide, tolcapone, entacapone, selegiline or rasagiline.

A further object of this invention resides in the use of a composition as defined above for the manufacture of a medicament for treating Parkinsonism, particularly PD.

In another embodiment, compositions or combination therapies of the invention can be used in conjunction with surgical therapy for PD such as deep brain stimulation. More particularly, surgical therapies are deep brain stimulation of the subthalamic nucleus or of the globus pallidus interna.

In this regard, the invention relates to a composition comprising at least one compound selected from the group consisting of acamprosate, baclofen, cinacalcet, mexiletine, sulfisoxazole, torasemide and tadalafil or salt(s), prodrug(s), derivative(s) of any chemical purity, or sustained-release formulation(s) thereof, for use in combination with deep brain stimulation of the subthalamic nucleus or of the globus pallidus interna, in the treatment of Parkinsonism, particularly PD.

PD motor symptoms can develop lately when the dopaminergic denervation of the striatum and lose of substantia nigra dopaminergic neurons are already widely occurring. Thus, the treatment of PD before motor symptoms appearance and in prevention is essential in order to alter the progression and course of the disease.

In this regard, in a preferred embodiment, any of the above methods, compositions or combination therapies can be used for the prevention, prophylaxis or retardation of symptoms provoked by or of the causes of PD.

The combination of early detection of non-motor symptoms, most particularly anosmia, with imaging techniques (Single-photon emission computed technology, Positron Emission Tomography) to assess changes in striatal dopamine transporter may be a suitable approach to identify at risk PD patients prior to the appearance of motor symptoms, thus allowing early start of neuroprotective therapy.

Some PD cases can be attributed to mutations within genes such as SNCA (alpha-synuclein), PRKN (parkin), LRRK2 (leucine-rich repeat kinase 2), PINK1 (PTEN-induced putative kinase 1), DJ-1 and ATP13A2 and eleven gene loci (PARK1-PARK11). In this regard, in a particular embodiment, the invention relates to the use of the above methods, compositions or combination therapies for the treatment of PD in a subject having a mutation in at least one of the following genes: SNCA, PRKN, LRRK2, PINK1, DJ-1, ATP13A2 and PARK1 to PARK11.

High concentrations exposure or chronic exposure to metals such as manganese, copper or lead, or chemicals, such as pesticides (e.g. paraquat, rotenone and maneb), are likely to cause Parkinsonism, particularly PD. In this regard, in a particular embodiment, the invention relates to the use of the above methods, compositions or combination therapies in the treatment of Parkinsonism, particularly PD, in a subject exposed, suspected to have been exposed or at risk of being exposed to chemicals or metals known to be risk factors for developing PD or related disorders.

In a preferred embodiment, the above methods, compositions or combination therapies can be used in a subject who is at risk of developing PD or symptoms associated with PD.

In another preferred embodiment, the above methods, compositions or combination therapies can be used for protecting a subject who is at risk of developing PD or symptoms associated with PD, from the death or degeneration of DA neurons.

Therapy according to the invention may be provided at home, the doctor's office, a clinic, a hospital's outpatient department, or a hospital, so that the doctor can observe the therapy's effects closely and make any adjustments that are needed.

The duration of the therapy depends on the stage of the disease being treated, age and condition of the patient, and how the patient responds to the treatment. The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers all drugs.

The administration of each drug of the combination may be by any suitable means that results in a concentration of the drug that, combined with the other component, is able to ameliorate the patient condition or efficiently treat the disease or disorder.

While it is possible for the drugs of the combination to be administered as the pure chemical, it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained, in any appropriate amount, in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), [30] and Encyclopedia of Pharmaceutical Technology [31]).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastrointestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropyl-methylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the drugs in a combination of this invention include, e.g., amounts that are effective for reducing Parkinson's disease symptoms, halting or slowing the progression of the disease once it has become clinically manifest, or prevention or reduction of the risk of developing the disease.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration is indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impairing cases, where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually low or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ¹⁄₁₀ of therapeutic doses. In particular examples, doses as low as ¹⁄₂₀, ¹⁄₃₀, ¹⁄₅₀, ¹⁄₁₀₀, or even lower, of therapeutic doses are used.

As mentioned above, this is likely due to a simultaneous activity of compositions of the invention on several targets involved in the alpha-synuclein aggregation network. In a particular embodiment such conjunction of molecular effects can further lead to synergistic combinations. Synergy may be assessed by methods known well known by those skilled in the art. For instance, synergy can be characterized by using a two way ANOVA to determine whether the interaction between each drugs is significant or not (i.e. synergy, [32]), or by calculating a combinatory index from the dose effect curves of each of the compounds alone and of their combinations [33, 34].

At such sub-therapeutic dosages, the compounds would exhibit no side effect, while the combination(s) according to the invention are fully effective in treating parkinsonism, more preferably PD.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of dosages of drugs (Quantity equivalent to active molecule) for use in the invention are provided below:

acamprosate: 1000 mg or less per day, preferably less than 500 mg per day, preferably less than 400 mg per day, more preferably less than 200 mg per day, more preferably less than 50 mg per day, or even less that than 10 mg per day; even more preferably from about 0.1 to 1000 mg per day, furthermore preferably between 0.5 mg and 100 mg, typically 0.8 mg per day, 2 mg per day, 20 mg per day, 40 mg per day, or 80 mg per day, such dosages being particularly suitable for oral administration, baclofen: 150 mg or less per day, preferably less than 100 mg per day, more preferably less than 50 mg per day, more preferably less than 30 mg per day, even more preferably between 0.01 mg and 30 mg per day, typically 12 mg per day, 24 mg per day, 30 mg per day, such dosages being particularly suitable for oral administration, such dosages being particularly suitable for oral administration, cinacalcet: 150 mg or less per day, preferably less than 100 mg per day, preferably less than 50 mg per day, more preferably less than 36 mg per day, and even more preferably between 0.01 and 25 mg per day, such dosages being particularly suitable for oral administration, mexiletine: 120 mg or less per day, preferably less than 60 mg per day, more preferably less than 30 mg per day, more preferably less than 15 mg per day, even more preferably between 6 and 15 mg per day, such dosages being particularly suitable for oral administration, torasemide: 4 mg or less per day, preferably less than 2 mg per day, more preferably less than 1 mg per day, more preferably less than 0.5 mg per day, and even more preferably between 0.05 and 0.5 mg per day, such dosages being particularly suitable for oral administration, sulfisoxazole: 800 mg or less per day, preferably less than 400 mg, more preferably less than 200 mg per day, more preferably less than 100 mg per day, even more preferably less than 20 mg per day, such dosages being particularly suitable for oral administration, tadalafil: 20 mg or less per day, preferably less than 10 mg per day, more preferably less than 4 mg per day, more preferably less than 2.5 mg per day, and even more preferably between 0.025 and 2.5 mg per day, such dosages being particularly suitable for oral administration, levodopa: 1.5 g or less per day, preferably less than 750 mg per day, more preferably less than 375 mg per day, even more preferably less than 100 mg per day, such dosages being particularly suitable for oral administration, rasagiline: 0.5 mg or less per day, preferably less than 0.25 mg per day, more preferably less than 0.1 mg per day, more preferably less than 0.05 mg per day, even more preferably between 0.005 and 0.05 mg per day, such dosages being particularly suitable for oral administration, selegiline: 5 mg or less per day, preferably less than 2.5 mg per day, more preferably less than 1 mg per day, more preferably less than 0.5 mg per day, even more preferably between 0.05 and 0.1 mg per day, such dosages being particularly suitable for oral administration.

In a particularly preferred embodiment, combinatorial therapies of the invention comprise administering between 0.4 mg and 50 mg of acamprosate and 6 mg to 15 mg baclofen, twice daily.

In an embodiment, combinatorial therapies the invention comprise administering 0.4 mg acamprosate and 6 mg baclofen, twice daily.

In a preferred embodiment, combinatorial therapies of the invention of the invention comprise administering 1 mg acamprosate and 15 mg baclofen, twice daily.

In yet another preferred embodiment, combinatorial therapies of the invention comprise administering 10 mg acamprosate and 6 mg baclofen, twice daily.

In another preferred embodiment, combinatorial therapies of the invention comprise administering 20 mg acamprosate and 12 mg baclofen, twice daily.

In still another embodiment, combinatorial therapies of the invention comprise administering 40 mg acamprosate and 12 mg baclofen, twice daily.

In still another embodiment, combinatorial therapies of the invention comprise administering 40 mg acamprosate and 30 mg baclofen, twice daily.

In another particular embodiment, besides comprising administering one of the above baclofen-acamprosate regimen, therapies of the invention also comprise administering levodopa or melevodopa either at their usual dose and regimen (i.e. as an add-on therapy) or even at a lower dose, from 1% up to 50% of those usually prescribed for the treatment of Parkinson's disease.

In a further particular embodiment, besides comprising administering one of the above baclofen-acamprosate regimen, therapies of the invention also comprise administering rasagiline or selegiline either at their usual dose and regimen (i.e. as an add-on therapy) or even at a lower dose, from 1% up to 50% of those usually prescribed for the treatment of PD.

When the composition comprises baclofen and acamprosate, these two compounds may be used in different ratios, e.g., at a weight ratio baclofen/acamprosate comprised between from 0.05 to 1000 (W:W), preferably between 0.05 to 100 (W:W), more preferably between 0.05 to 62.5 (W:W), even more between preferably 0.3 to 15 (W:W). Typically such weight ratio baclofen/acamprosate is 0.3, 0.6, 0.75, 1.2, 3.1, 12, 15, 25 or 62.5.

It will be understood that the amount of the drug or the drug combination actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

All animal procedures have been conducted in compliance to the National Institute of Health (NIH) guidelines for the care and use of laboratory animals, and approved by the National Animal Experiment Board.

A—Prevention of Glutamate Toxicity on Neuronal Cells

Glutamate toxicity is involved in the pathogenesis of Parkinson's disease. In this set of experiment, candidate compounds have been tested for their ability to prevent or reduce the toxic effects of glutamate toxicity on neuronal cells. The drugs are first tested individually, followed by assays of their combinatorial action.

Neuronal Cell Preparation

The efficacy of drug combinations of the invention is assessed on primary cortical neuron cells.

Rat cortical neurons were cultured as described by Singer et al. [35]. Briefly pregnant female rats of 15 days gestation were killed by cervical dislocation (Rats Wistar) and the foetuses were removed from the uterus. The cortex was removed and placed in ice-cold medium of Leibovitz (L15) containing 2% of Penicillin 10.000 U/ml and Streptomycin 10 mg/ml and 1% of bovine serum albumin (BSA). Cortices were dissociated by trypsin for 20 min at 37° C. (0.05%). The reaction was stopped by the addition of Dulbecco's modified Eagle's medium (DMEM) containing DNase1 grade II and 10% of foetal calf serum (FCS). Cells were then mechanically dissociated by 3 serial passages through a 10 ml pipette and centrifuged at 515 g for 10 min at +4° C. The supernatant was discarded and the pellet of cells was re-suspended in a defined culture medium consisting of Neurobasal supplemented with B27 (2%), L-glutamine (0.2 mM), 2% of PS solution and 10 ng/ml of BDNF. Viable cells were counted in a Neubauer cytometer using the trypan blue exclusion test. The cells were seeded at a density of 30 000 cells/well in 96 well-plates (wells were pre-coated with poly-L-lysine (10 µg/ml)) and were cultured at +37° C. in a humidified air (95%)/CO2 (5%) atmosphere.

Glutamate Toxicity Assays

The neuroprotective effect of compounds is assessed by quantification of the neurite network (Neurofilament immunostaining (NF) which specifically reveals the glutamatergic neurons).

After 12 days of neuron culture, drugs of the candidate combinations are solved in culture medium (+0.1% DMSO). Candidate combinations are then pre-incubated with neurons for 1 hour before the glutamate injury. One hour after incubation with, glutamate is added for 20 min, to a final concentration of 40 µM, in presence of candidate combinations, in order to avoid further drug dilutions. At the end of the incubation, medium is changed with medium with candidate combination but without glutamate. The culture is fixed 24 hours after glutamate injury. MK801 (dizocilpine-hydrogen maleate, 77086-22-7-20 µM) is used as a positive control.

After permeabilization with saponin (Sigma), cells are blocked for 2 h with PBS containing 10% goat serum, then the cells are incubated with mouse monoclonal primary antibody against Neurofilament antibody (NF, Sigma). This antibody is revealed with Alexa Fluor 488 goat anti-mouse IgG.

Nuclei of cells are labeled by a fluorescent marker (Hoechst solution, SIGMA), and neurite network quantified. Six wells per condition are used to assess neuronal survival in 3 different cultures.

Results

All of the tested drug combinations give a protective effect against glutamate toxicity for cortical neuronal cells. Results are shown in Table 2 below.

Figure 2:
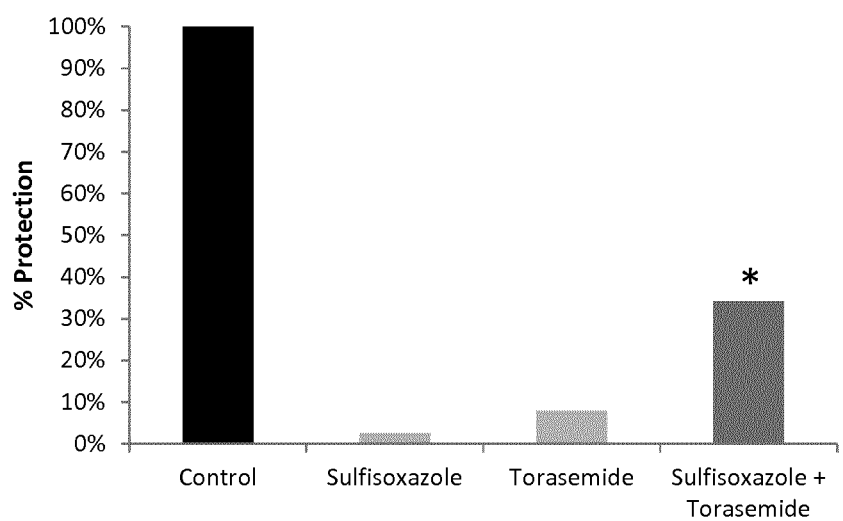
FIG. 2: Effect of sulfisoxazole and torasemide combination therapy against glutamate toxicity on neuronal cortical cells. The glutamate intoxication is significantly prevented by the combination of sulfisoxazole (6.8 nM) and torasemide (400 nM) whereas, at those concentrations, sulfisoxazole and torasemide alone have no significant effect on intoxication.*: $p<0.001$, significantly different from glutamate intoxication; (ANOVA+Dunett's Post-Hoc test).
Figure 3:
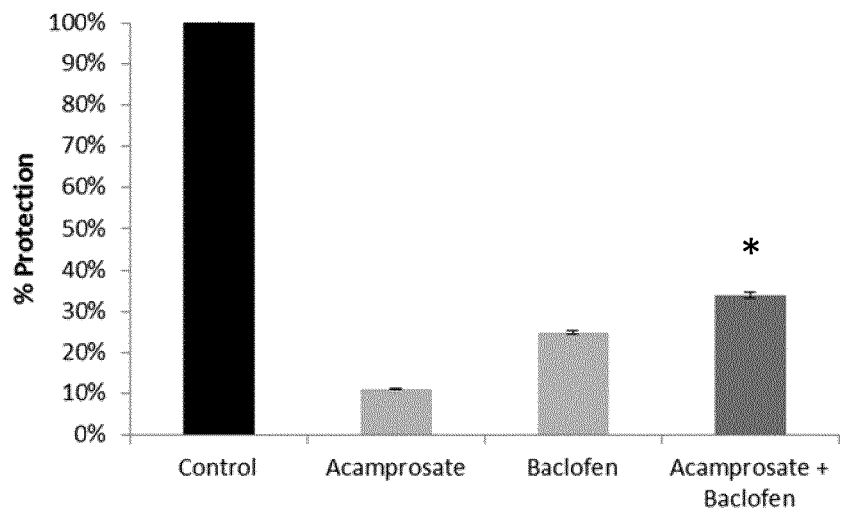
FIG. 3: Effect of baclofen and acamprosate combination therapy against glutamate toxicity on neuronal cortical cells. The glutamate intoxication is significantly prevented by the combination of baclofen (400 nM) and acamprosate (1.6 nM) whereas, at those concentrations, baclofen and acamprosate alone have no significant effect on intoxication. *: $p<0.001$, significantly different from glutamate intoxication; (ANOVA+Dunett's Post-Hoc test).

As exemplified in FIGS. 1 to 3, combinations of the invention strongly protect neurons from glutamate toxicity under experimental conditions described above. It is noteworthy that an effective protection is noticed using drug concentrations at which drugs used alone have no significant or lower protective effect.

Indeed, as exemplified in FIG. 1, mexiletine-cinacalcet combination efficiently protects neuronal cells from glutamate toxicity, whereas no protection is afforded by the single drugs. Baclofen-acamprosate (FIG. 3) combination gives a protective effect against glutamate toxicity for cortical neuronal cells. Combination of baclofen and acamprosate induces an improvement of more than 200% compared to acamprosate alone and of more than 47% compared to baclofen used alone.

TABLE 2

| Drug Combination | Neuroprotective effect against glutamate toxicity |
|---|---|
| baclofen and torasemide | + |
| baclofen-acamprosate-torasemide | + |
| mexiletine and cinacalcet | + |
| sulfisoxazole and torasemide | + |
| baclofen and acamprosate | + |
| acamprosate and cinacalcet | + |
| baclofen and cinacalcet | + |

B—Protective Effect Against Ischemia/Hypdxia Induced Neuronal Cell Death.

Rat Neuronal Cortical Cells Preparation

Cells are prepared as previously.

Oxygen and Glucose Deprivation Assays (In Vitro Model of Ischemia)

The neuroprotective effect of compounds is assessed by quantification of the neurite network using MAP2 antibody. Riluzole, a neuroprotective drug, (Riluteck®, 5 µM) is used as positive control.

After 10 days of neuron culture, candidate drugs are solved in culture medium (+0.1% DMSO) and then pre-incubated with neurons for 1 hour before the oxygen and glucose deprivation. One hour after candidate drug incubation, the medium is removed and fresh medium without glucose is added. This medium is composed by DMEM without glucose (Invitrogen) supplemented with 2% B27, 0.2 mM L-glutamine, 1% PS solution, 10 ng/ml of BDNF. The cells are transferred into an anaerobic incubator with 95% $N_2$ and 5% $CO_2$ at 37° C.

After 2 hours, 25 mM of D-Glucose will be added in culture medium and cells are transferred in classic incubator with 95% air/5% $CO_2$ at 37° C. After 24 hours of oxygen glucose reperfusion, cells are fixed by a cold solution of alcohol/acetic acid during 5 minutes.

After permeabilization with saponin (Sigma), cells are blocked for 2 hours with PBS containing 10% goat serum, then the cells are incubated with mouse monoclonal primary antibody against MAP2 (MAP2, Sigma). These antibodies are revealed with Alexa Fluor 488 goat anti-mouse IgG (Molecular probe).

Nuclei of cells are labelled by a fluorescent marker (Hoechst solution, SIGMA). Six wells per condition are used to assess neuronal survival in 3 different cultures.

For each condition 2×10 pictures per well are taken and analyzed using InCell Analyzer™ 1000 (GE Healthcare) with 20× magnification.

Results

As shown in Table 3 below, all of the claimed drug combinations give a protective effect against ischemia/hypoxia induced cell death for cortical neuronal cells.

TABLE 3

| Drug Combination | Protective effect against ischemia/hypoxia |
|---|---|
| baclofen and torasemide | + |
| baclofen - acamprosate - torasemide | + |
| mexiletine and cinacalcet | + |
| sulfisoxazole and torasemide | + |
| baclofen and acamprosate | + |
| acamprosate and cinacalcet | + |
| baclofen and cinacalcet | + |

Figure 4:
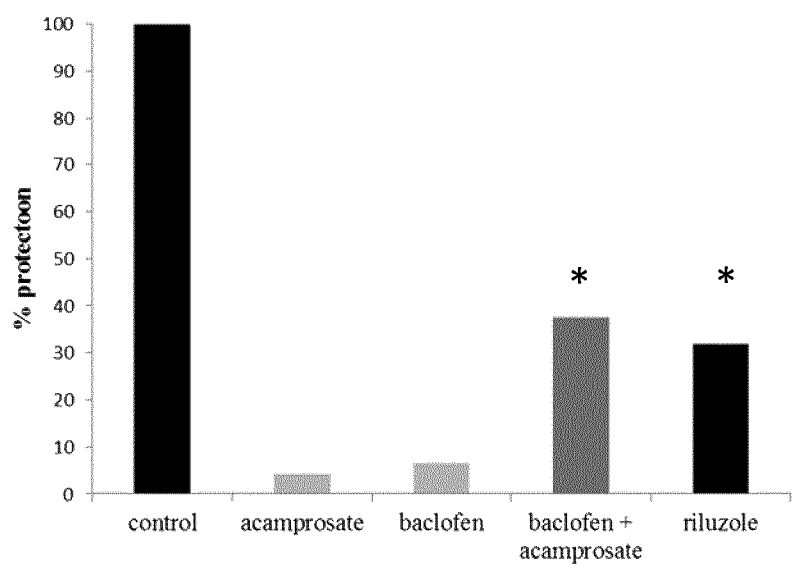
FIG. 4: Protective effect of baclofen and acamprosate combination against ischemic injury. Whereas no significant protection is obtained when baclofen (80 nM) or acamprosate (0.32 nM) are used alone, a significant protection (*: $p<0.0001$) is observed for the combination of the two drugs, at the same concentrations.
Figure 5:
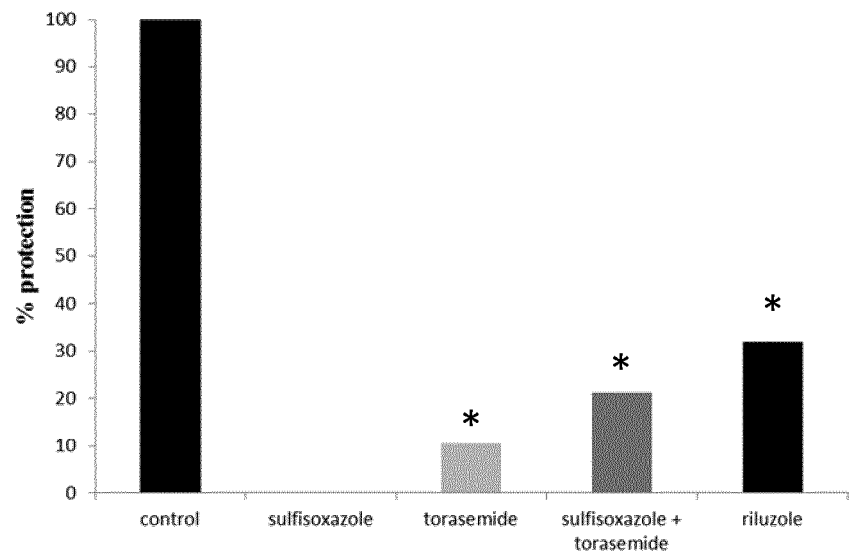
FIG. 5: Protective effect of torasemide and sulfisoxazole combination against ischemic injury. The combination of sulfisoxazole (1.36 nM) and torasemide (80 nM) induces a significant protection (*: $p<0.0001$), 110% higher than the protection obtained using torasemide alone, whereas no protection is obtained when sulfisoxazole is used alone.
Figure 6:
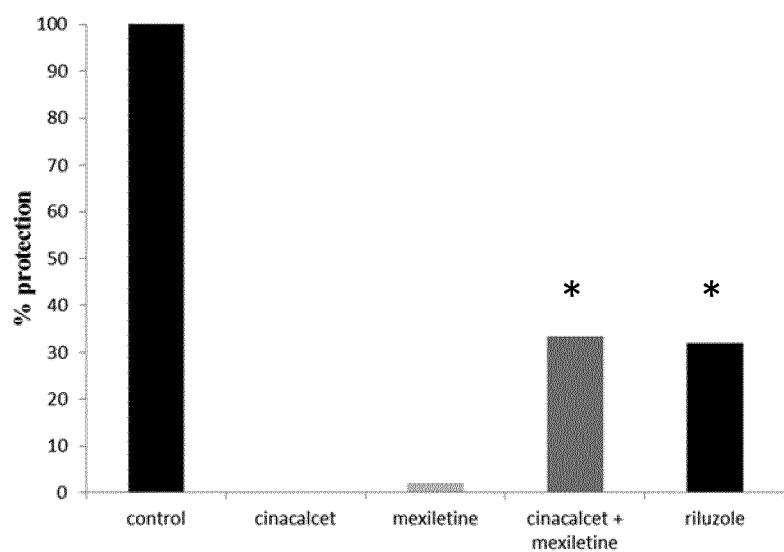
FIG. 6: Protective effect of cinacalcet and mexiletine combination against ischemic injury. No significant protection is observed when cinacalcet (64 pM) or mexiletine (25.6 pM) are used alone, whereas a significant protection (*: $p<0.0001$) is observed for the combination of the two drugs, at the same concentrations.
Figure 7:
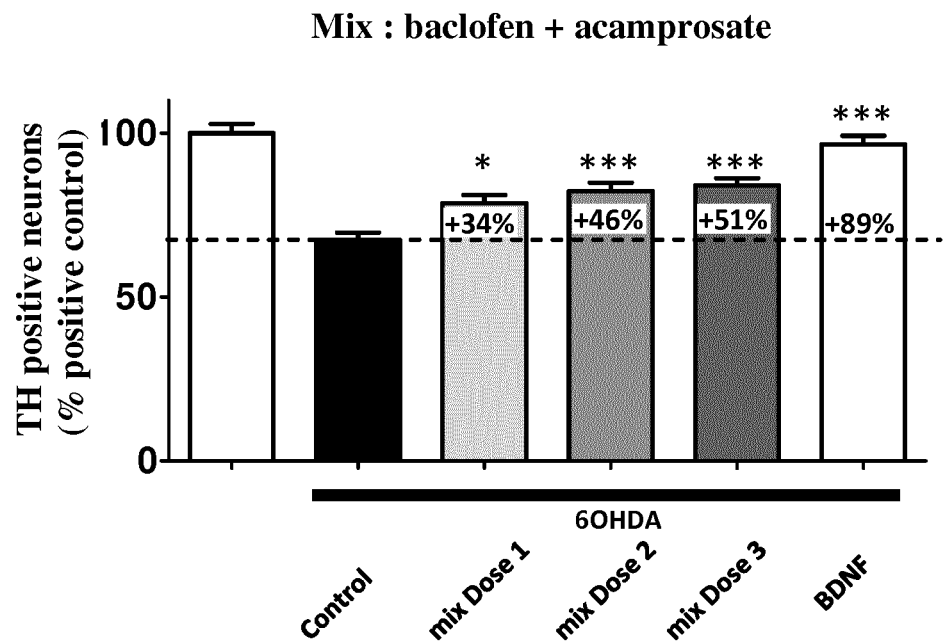
FIG. 7: Effect of baclofen and acamprosate combination therapy against 6-OHDA injury on dopaminergic neuronal cells. The protection increases correlatively with concentration of mixes. A significant protective effect is observed with an increase in TH neurons survival by 34% with dose 1 (16 nM and 64 pM respectively), by 46% with dose 2 (80 nM and 144 pM) and by 51% with dose 3 (400 nM and 1600 pM) (***: $p<0.0001$; *: $p<0.001$: significantly different from 6-OHDA intoxicated cells (ANOVA+Dunett's test)).
Figure 8:
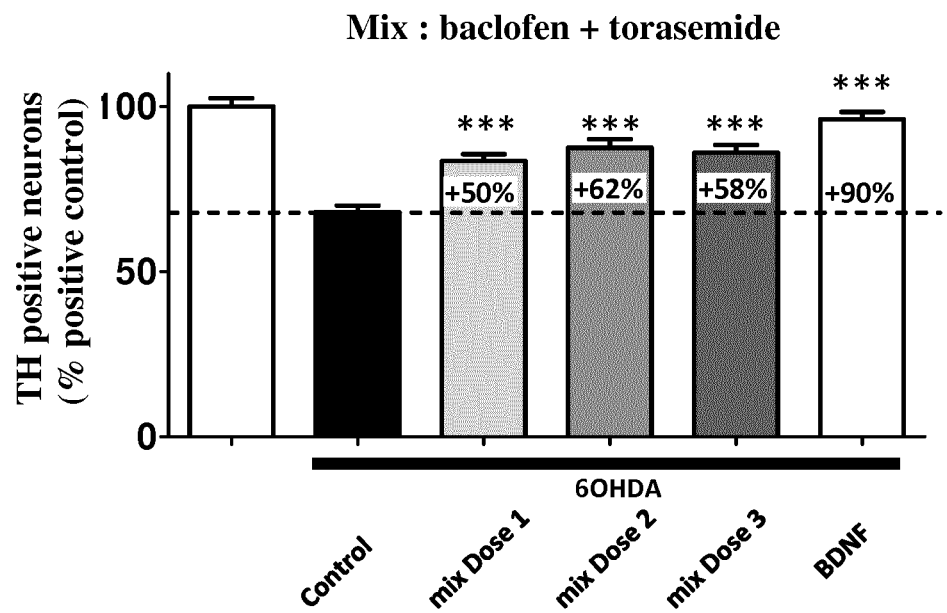
FIG. 8: Effect of baclofen and torasemide combination therapy against 6-OHDA injury on dopaminergic neuronal cells. A significant protective effect is observed with an increase in TH neurons survival by 50% with low dose 1 (80 nM and 16 nM respectively), by 62% with the middle dose 2 (240 nM and 48 nM) and by 58% with high dose 3 (720 nM and 144 nM) (***: $p<0.0001$: significantly different from 6-OHDA intoxicated cells (ANOVA+Dunett's test)).
Figure 9:
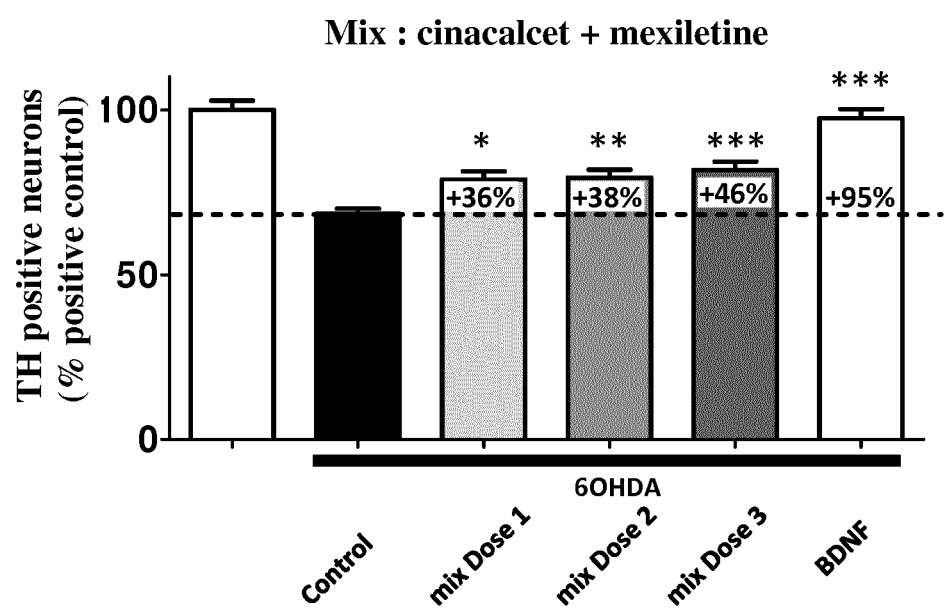
FIG. 9: Effect of cinacalcet and mexiletine combination therapy against 6-OHDA injury on dopaminergic neuronal cells. All the tested concentrations afford a significant protection against 6-OHDA. Indeed, a significant protective effect is observed with an increase in TH neurons survival by 36% with dose 1 (64 pM and 5 pM respectively), by 38% with the dose 2 (64 pM and 26 pM) and by 46% with dose 3 (1600 pM and 64 pM) (***: $p<0.0001$; *: $p<0.001$: significantly different from 6-OHDA intoxicated cells (ANOVA+Dunett's test)).

FIGS. 4-6 further show that the combination treatments of the invention strongly protect neurons from oxygen and glucose deprivation. As shown in FIGS. 4-6, an effective protection is observed using drug concentrations at which drugs, alone, have no significant protective effect. For example, a significant protective effect of baclofen (80 nM)/acamprosate (0.32 nM) combination or cinacalcet (64 pM)/mexiletine (25.6 pM) combination or torasemide (80 nM)/sulfisoxazole (1.36 nM), in ischemia is observed, while no significant protection is obtained when baclofen, acamprosate, cinacalcet, mexiletine, torasemide and sulfisoxazole are used alone, at the same concentrations.

These results therefore demonstrate a potent and synergistic effect of the combination therapies on oxidative stress and mitochondrial dysfunction or apoptosis which are underlie under ischemic conditions as well as PD.

C— Neuro-Protective Effect of Drugs Against 6-OHDA Injury on Dopaminergic Neurons 6-hydroxydopamine (6-OHDA) is a neurotoxic drug which selectively initiates neuronal degeneration of dopaminergic neurons by generating reactive oxygen species and mitochondrial respiratory dysfunction which are thought to mirror events occurring in parkinsonian brain. 6-OHDA toxicity is commonly used in vitro and in vivo to study Parkinsonism.

Culture of Mesencephalic Dopaminergic Neurons

Rat dopaminergic neurons were cultured as described by Schinelli et al. [36]. Pregnant female rats of 15 days gestation were killed by cervical dislocation (Rats Wistar; Janvier) and the foetuses removed from the uterus. The embryonic midbrains were removed and placed in ice-cold medium of Leibovitz (L15; PanBiotech) containing 2% of Penicillin-Streptomycin (PS; PanBiotech) and 1% of bovine serum albumin (BSA; PanBiotech). Only the ventral portions of the mesencephalic flexure were used for the cell preparations as this is the region of the developing brain rich in dopaminergic neurons. The midbrains were dissociated by trypsinisation for 20 min at 37° C. (Trypsin EDTA 1×; PanBiotech). The reaction is stopped by the addition of Dulbecco's modified Eagle's medium (DMEM; PanBiotech) containing DNAase I grade II (0.1 mg/ml; PanBiotech) and 10% of foetal calf serum (FCS; Invitrogen). Cells were then mechanically dissociated by 3 passages through a 10 ml pipette and centrifuged at 180×g for 10 min at +4° C. on a layer of BSA (3.5%) in L15 medium. The supernatant was discarded and the cells of pellet were re-suspended in a defined culture medium consisting of Neurobasal (Invitrogen) supplemented with B27 (2%; Invitrogen), L-glutamine (2 mM; PanBiotech) and 2% of PS solution and 10 ng/ml of Brain-derived neurotrophic factor (BDNF, PanBiotech) and 1 ng/ml of Glial-Derived Neurotrophic Factor (GDNF, PanBiotech). Viable cells were counted in a Neubauer cytometer using the trypan blue exclusion test. The cells were seeded at a density of 40 000 cells/well in 96 well-plates (pre-coated with poly-L-lysine (Greiner)) and are cultured at 37° C. in a humidified air (95%)/CO2 (5%) atmosphere. Half of the medium was changed every 2 days with fresh medium. Five to six percent of the neuronal cell population were dopaminergic neurons.

6-OHDA and Test Compounds Exposure

On day 6 of culture, the medium was removed and fresh medium was added, without or with 6-OHDA at the following concentrations: 20 μM during 48 hours diluted in control medium. Test compounds were pre-incubated for 1 h before the 6-OHDA application during 48 hours.

End Point Evaluation: Measure of Total Number of Tyrosine Hydroxylase (TH) Positive Neurons After 48 hours of intoxication with 6-OHDA, cells were fixed by a solution of 4% paraformaldehyde (Sigma) in PBS, pH=7.3 for 20 min at room temperature. The cells were washed again twice in PBS, and then permeabilized and non-specific sites were blocked with a solution of PBS containing 0.1% of saponin (Sigma) and 1% FCS for 15 min at room temperature. Then, cells were incubated with Monoclonal Anti-Tyrosine Hydroxylase antibody produced in mouse (TH, Sigma) at dilution of 1/1000 in PBS containing 1% FCS, 0.1% saponin, for 2 hours at room temperature. These antibodies were revealed with Alexa Fluor 488 goat anti-mouse IgG (Molecular Probes) at the dilution 1/800 in PBS containing 1% FCS, 0.1% saponin, for 1 hour at room temperature.

For each condition, 2×10 pictures (representing ~80% of total well area) per well were taken using InCell Analyzer™ 1000 (GE Healthcare) with 10× magnification. All images were taken in the same conditions. Analysis of the number of TH positive neurons were done using Developer software (GE Healthcare).

Data are expressed in percentage of control conditions (no intoxication, no 6-OHDA=100%) in order to express the 6-OHDA injury. All values are expressed as mean+/−SEM (s.e. mean) of the 3 cultures (n=6 wells per condition per culture). Statistical analyses consist in an ANOVA followed by the Dunnett's and PLSD Fisher's tests when it was allowed using Statview software version 5.0.

Results

A neuroprotective effect is observed for combinations of the invention in TH neurons survival test after 48 hour 6-OHDA injury on dopaminergic neurons.

A 48 h 6-OHDA (20 μM) incubation with mesencephalic neurons produced a significant intoxication of dopaminergic neurons (around −33% of TH neurons) in all the experiments (control, FIGS. 7-9,12-14).

BDNF was used as a positive control. One hour of BDNF pre-treatment at 1.85 nM significantly protected the dopaminergic neurons from this 6-OHDA injury.

As shown in table 4 below, all of the claimed drug combinations give a protective effect against 6-OHDA injury in dopaminergic neuronal cells.

TABLE 4

| Drug Combination | Protective effect against 6-OHDA injury in dopaminergic neuronal cells |
| --- | --- |
| baclofen and torasemide | + |
| baclofen-acamprosate-torasemide | + |
| mexiletine and cinacalcet | + |
| sulfisoxazole and torasemide | + |
| baclofen and acamprosate | + |
| acamprosate and cinacalcet | + |
| baclofen and cinacalcet | + |
| cinacalcet and tadalafil | + |

As shown in FIGS. 7-9 and 12-14, baclofen-acamprosate, baclofen-torasemide, mexiletine-cinacalcet, acamprosate-cinacalcet, cinacalcet-tadalafil successfully protect dopaminergic neurons from 6-OHDA toxicity.

Notably, baclofen-acamprosate combination is shown effective in protecting, in vitro, dopaminergic neurons for a large range of concentrations of baclofen (from 16 nM to 400 nM) and acamprosate (from 4 pM to 1600 pM).

Moreover inventors have been able to draw dose-effect curves for each baclofen, acamprosate, cinacalcet and tadalafil (not shown) which further allow to determine the combinatory index (CI) of the combination of these drugs according to Loewe [33, 34]. A combinatory index below 1 characterizes synergy between drugs within a given combination.

Figure 12:
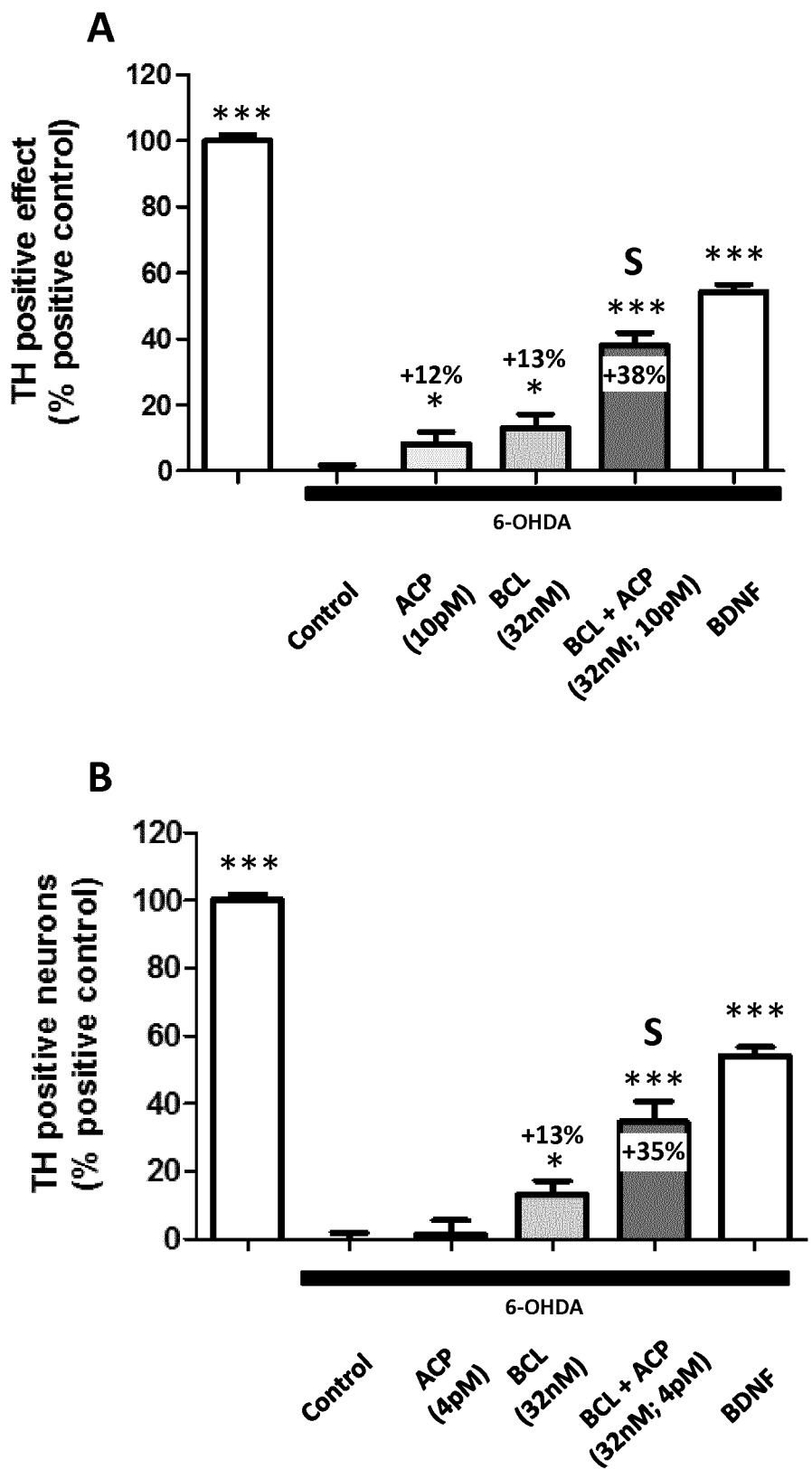
FIG. 12: Baclofen (BCL) and acamprosate (ACP) combination acts synergistically in protecting dopaminergic neuronal cells from 6-OHDA injury. A: Baclofen, at a dose as low as 32 nM, when combined with acamprosate, at a dose as low as 10 pM, strongly protects dopaminergic neuron from 6-OHDA injury (+38% survival), while single drugs at the same dose have low effect. B: Baclofen, 32 nM, combined with acamprosate at an even lower dose, 4 pM, also strongly protects cortical neuron from 6-OHDA injury (+35%), while single drugs at the same dose have low effect. ***: $p<0.001$; *: $p<0.05$, significantly different from 6-OHDA intoxicated cells (ANOVA+Dunett's test). S: synergy.

As illustrated in FIG. 12, the baclofen-acamprosate mix displaying a synergistic activity in the above glutamate toxicity and ischemia in vitro models, is also found as having a synergistic activity in the 6-OHDA toxicity model. For example, baclofen at 32 nM when combined with acamprosate at either 4 pM or 10 pM show a synergistic protective activity (S, FIG. 12) on 6-OHDA intoxicated dopaminergic neuronal cells, with a CI=0.4 or 0.5 respectively.

Figure 13:
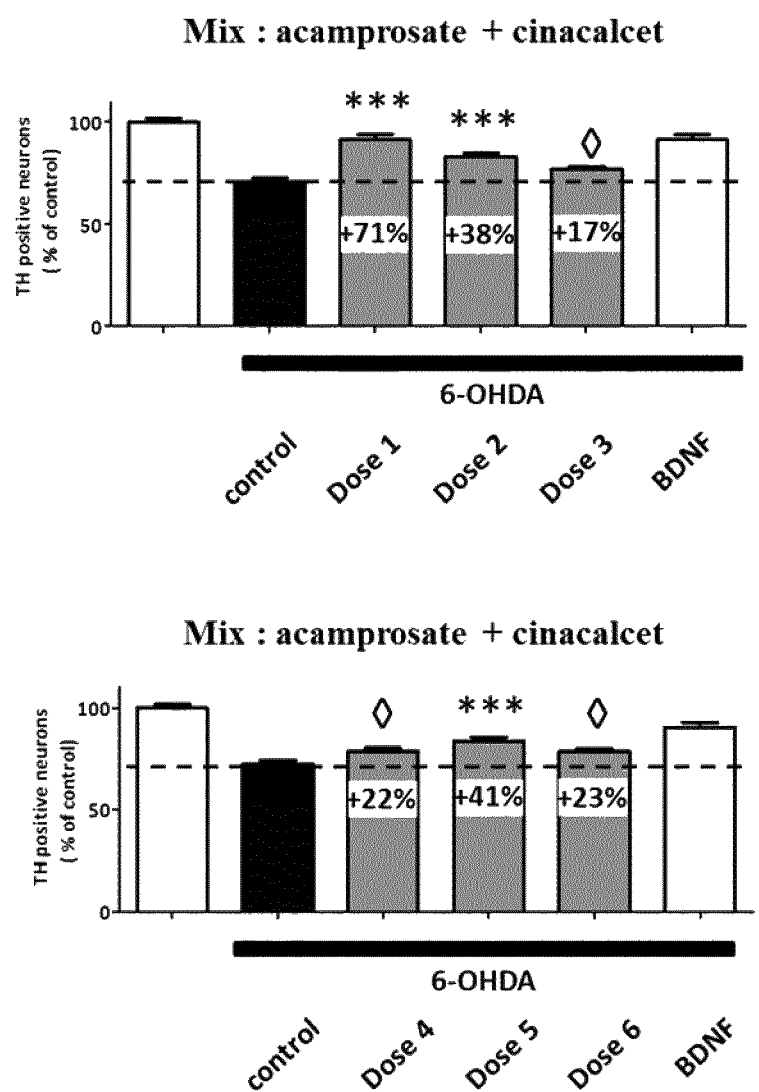
FIG. 13: Effect of acamprosate and cinacalcet combination therapy against 6-OHDA injury on dopaminergic neuronal cells. The tested concentrations afford a significant protection against 6-OHDA. Indeed, a significant protective effect is observed with an increase in TH neurons survival of 17% to 73% is observed. At each of these concentrations, the combination exerts a synergistic protective effect. ***: $p<0.001$; significantly different from 6-OHDA intoxicated cells (ANOVA+Dunett's test); 0: $<0.05$: significantly different from 6-OHDA intoxicated (Student's test).

Tested combinations of acamprosate-cinacalcet at different drug concentrations were also found to have a synergistic protective effect against 6-OHDA induced toxicity. Their neuroprotective effect is particularly important, especially when considering the very low concentrations of the drugs, as illustrated in FIG. 13 and table 5. Combinatory indexes related to the different tested compositions are, by far, below the limit of 1 which denotes a strong synergistic protective effect of the mix acamprosate-cinacalcet on dopaminergic neurons (table 5).

TABLE 5

| Mix acamprosate-cinacalcet | | Protection | Combinatory |
| --- | --- | --- | --- |
| Acamprosate | Cinacalcet | (% of control) | index |
| Dose 1 | 2 pM | 1.6 nM | +71% | 0.00016 |
| Dose 2 | 2 pM | 8 nM | +38% | 0.00848 |
| Dose 3 | 2 pM | 40 nM | +17% | 0.344 |
| Dose 4 | 10 pM | 1.6 nM | +22% | 0.138 |
| Dose 5 | 4 pM | 1.6 nM | +41% | 0.0024 |
| Dose 6 | 4 pM | 40 nM | +23% | 0.276 |

Figure 14:
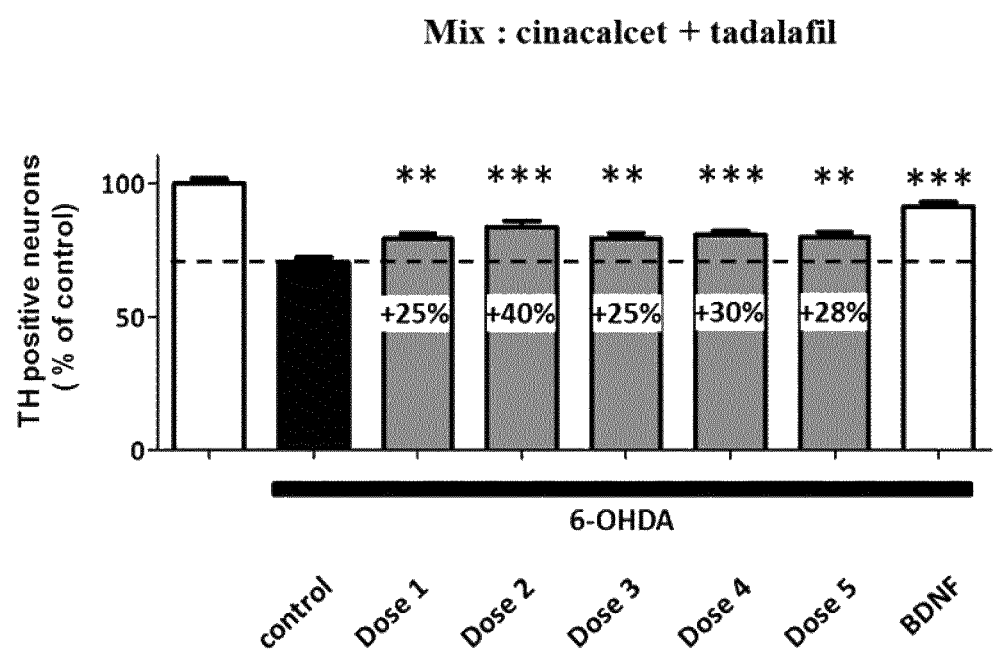
FIG. 14: Effect of cinacalcet and tadalafil combination therapy against 6-OHDA injury on dopaminergic neuronal cells. Combination therapy affords a significant protection at different drug concentrations. For the different doses presented, drugs act synergistically to confer protection. (*: $p<0.001$; : $p<0.01$, significantly different from 6-OHDA intoxicated cells (ANOVA+Dunett's test)).

Tested combinations of cinacalcet-tadalafil were also found efficient in protecting dopaminergic neurons from 6-OHDA toxicity. This protective effect against 6-OHDA induced toxicity has been found synergistic for various doses of individual drugs. Their neuroprotective effect is illustrated in FIG. 14. Combinatory indexes related to the different tested compositions are below the limit of 1 which denotes a strong synergistic protective effect of the mix cinacalcet-tadalafil on dopaminergic neurons (table 6).

TABLE 6

| Mix cinacalcet-tadalafil | | Protection | Combinatory |
| --- | --- | --- | --- |
| cinacalcet | tadalafil | (% of control) | index |
| Dose 1 | 1.6 nM | 1 nM | +25% | 0.676 |
| Dose 2 | 1.6 nM | 10 nM | +40% | 0.781 |
| Dose 3 | 8 nM | 1 nM | +25% | 0.651 |
| Dose 4 | 40 nM | 0.5 nM | +30% | 0.336 |
| Dose 5 | 40 nM | 1 nM | +28% | 0.692 |
| Dose 6 | 40 nM | 10 nM | +30% | N/A |
| Dose 7 | 8 nM | 10 nM | +35% | N/A |

N/A: not available

D—Effects on Dopaminergic Neuronal Loss In Vivo and on Motor Symptoms

1) Improvement of Akinesia In Vivo

Animal Husbandry and Surgical Procedure

Wistar rats (5 weeks) were used after an acclimatization period of at least 5 days. Surgery was performed under ketamine (50 mg/kg) and xylazine (10 mg/kg). Animals received an unilateral injection of 12 μg of 6-OHDA (sigma Aldrich) dissolved in 6 μl of 0.9% sterile NaCl containing 0.1% ascorbic acid (to protect 6-OHDA from oxidation), at the flow rate of 1 μl/min, in the left substantia nigra pars compacta. The stereotaxic coordinates of the injection site will be: anteroposterior+2.2 mm, lateral 2.0 mm, dorsoventral+3 mm with the incisor bar at +5.0 mm above the interaural plane, according to the rat stereotaxic atlas by De Groot (1959) [37].

Drug(s) Treatment

The first administration of treatment or vehicle has been performed the day before the stereotaxic injection of 6-OHDA (for the lesion groups) or vehicle and all along the 15 days preceding the behavioral tests. Rats of the reference treatment group were administered with a combination of L-DOPA (8 mg/kg) and benserazide (a peripheral DPA decarboxylase inhibitor, 12.5 mg/kg). During the study and for each animal, the volume of per os administrations was determined on the basis of the mean body weight of the animals of the corresponding group. Body weights will be determined twice a week and the volume of administration will thus be adjusted consequently.

Vehicles and compounds have been administered twice a day (i.e. bid: bis in die) through the oral route, in the morning and in the afternoon; eight hours (+/−30 min) separated the two administrations around 9:30 AM and around 17:30 PM.

On the day of behavioral tests, the drugs have been administered around 1 hour for L-DOPA treated group and around 2 hour (+/−15 min) for the drug combinations before the behavioral test, for each animal.

Behavioral Testing

Each test was performed before surgery (2 or 3 days before) to determine the basal level value. Assessment of behavioral functions is performed 15 days after surgical injection of 6-OHDA using the two different tests.

Initiation Time Test (ITT):

The animal was hold by a trained technician in front of a plane surface. Only one of the two forelimbs was left free to move. The time that was necessary to initiate the movement toward the plane surface has been recorded using 180 sec as break-off point [38].

Stepping Test (ST):

The rat was hold by the experimenter and only one of the two forelimbs have been left free to move above a plane surface. The other hand fixed the forelimb not to be monitored with one paw touching the table. The animal has then been moved slowly backward or forward (5 sec for 0.9 m) by the experimenter. The number of adjusting steps was counted for the right paw [38].

Cylinder Test (CT):

The rat was placed in plexiglass cylinder and, immediately after, videotaped for 15 min to examine the symmetry/asymmetry of their forepaws use during explorative behavior in this new environment. The numbers of contacts made on the cylinder wall during this period with the ipsilateral paw, the contralateral paw, and with both paws (double contacts) will be determined and expressed as a percentage of the total number of contacts [39, 40].

Results

In vivo assays were carried out with drug combinations of the invention. Tested drug combinations of the invention induced a significant improvement either in the initiation time test or stepping test (table 7).

TABLE 7

| Drug Combination | Protective effect against 6-OHDA induced akinesia |
|---|---|
| baclofen and torasemide | + |
| baclofen - acamprosate - torasemide | + |
| mexiletine and cinacalcet | + |
| sulfisoxazole and torasemide | + |
| baclofen and acamprosate | + |
| acamprosate and cinacalcet | + |
| baclofen and cinacalcet | + |
| cinacalcet and tadalafil | + |

Figure 10:
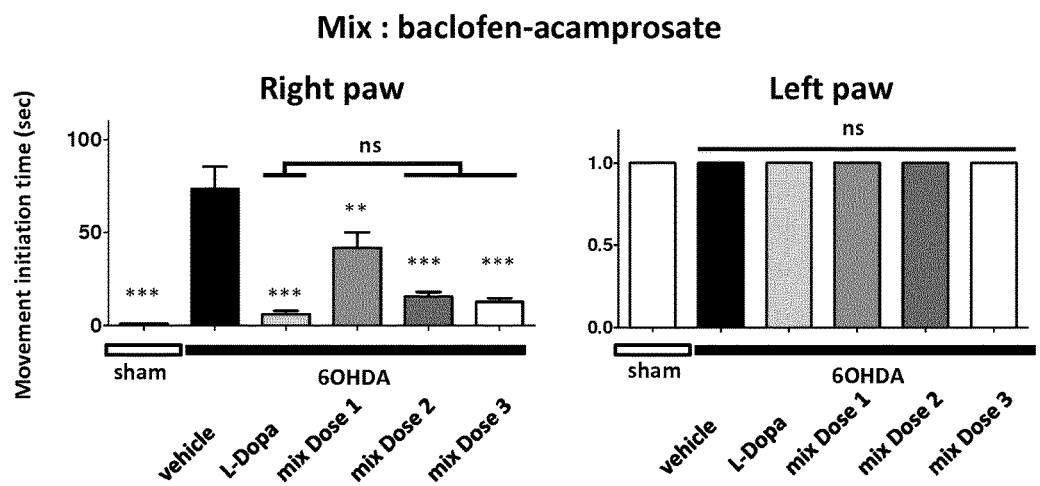
FIG. 10: Initiation time test, effect of baclofen and acamprosate combination therapy against 6-OHDA stereotaxic lesion in the left substantia nigra pars compacta. Left paw: no significant change. Right paw: 6-OHDA injection strongly prolonged initiation time as a result of death of neurons in the left substantia nigra. Baclofen-acamprosate treatment strongly protects from 6-OHDA induced akinesia and this from the weakest dose 1 (baclofen-acamprosate dose 1: 0.6 mg/kg bid and 0.04 mg/kg bid respectively; dose 2: 1.5 mg/kg bid and 0.1 mg/kg bid; dose 3: 3.75 mg/kg bid and 0.25 mg/kg bid; *: $p<0.0001$; : $p<0.001$: significantly different from 6-OHDA intoxicated cells (ANOVA+Dunett's test)); ns: no significant difference between data.
Figure 11:
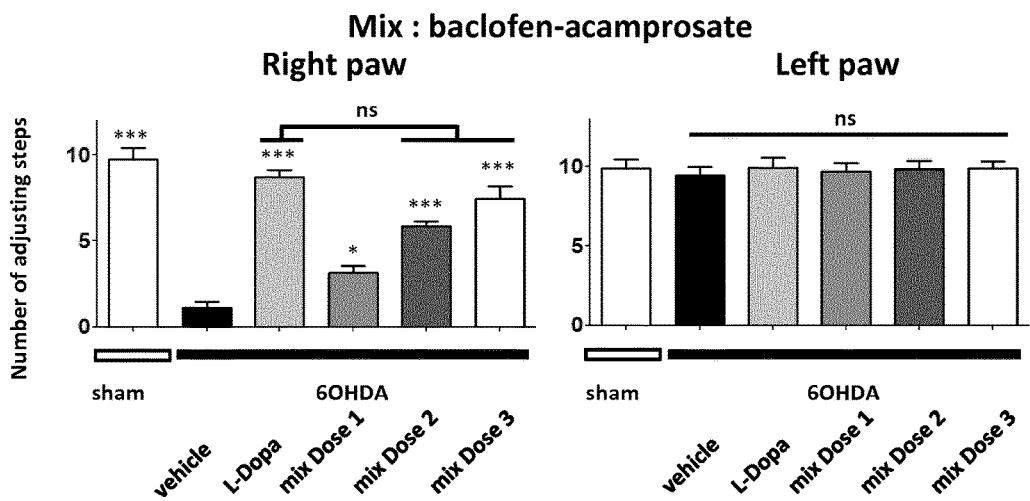
FIG. 11: Reaction time test, effect of baclofen and acamprosate combination therapy against 6-OHDA stereotaxic lesion in the left substantia nigra pars compacta. Left paw: no significant change. Right paw: 6-OHDA injection strongly prolonged reaction time as a result of death of neurons in the left substantia nigra. Baclofen-acamprosate treatment strongly protects from 6-OHDA induced akinesia and this from the weakest dose 1. Dose 2 and 3 almost fully alleviate 6-OHDA induced akinesia (baclofen-acamprosate dose 1: 0.6 mg/kg bid and 0.04 mg/kg bid; dose 2: 1.5 mg/kg bid and 0.1 mg/kg bid; dose 3: 3.75 mg/kg bid and 0.25 mg/kg bid; ***: $p<0.0001$; *: $p<0.05$: significantly different from 6-OHDA intoxicated cells (ANOVA+Dunett's test)); ns: no significant difference between data.

As exemplified in FIGS. 10 and 11, drug combinations of the invention strongly protect rats from 6-OHDA stereotaxic lesions. Noteworthy, treatment with baclofen-acamprosate combination results in an almost full alleviation of akinesia in the stepping test and in the initiation test, in a dose dependent manner.

Figure 15:
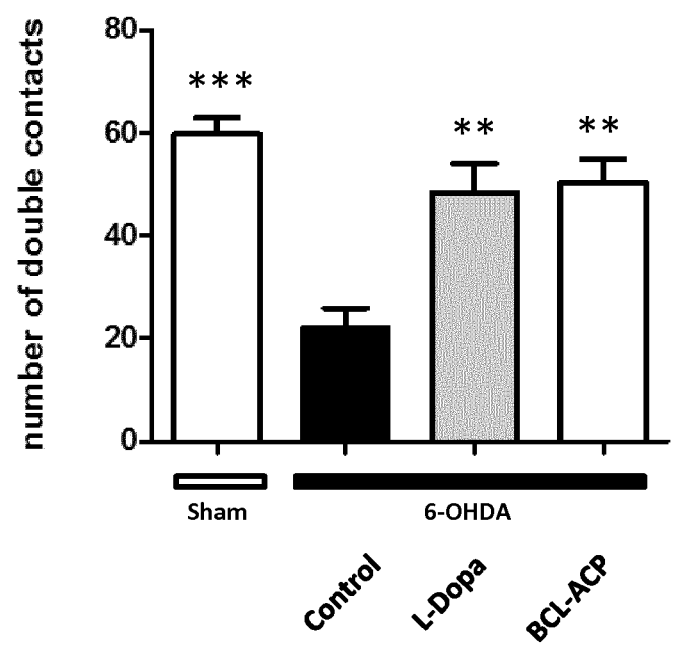
FIG. 15: Cylinder test, effect of baclofen and acamprosate combination therapy against 6-OHDA stereotaxic lesion in the left substantia nigra pars compacta. 6-OHDA injection strongly decreased the number of double contacts as a result of death of neurons in the left substantia nigra (control, black bar). Baclofen-acamprosate treatment (3.75 mg/kg bid and 0.25 mg/kg bid, respectively) strongly protects rats from 6-OHDA induced akinesia, the number of contacts is significantly enhanced when compared to control. *: $p<0.001$; : $p<0.01$: significantly different from 6-OHDA intoxicated cells (ANOVA+Dunett's test)).

This effect on the combinations of the invention on akinesia was also assessed in a different test (cylinder test) also used to evaluate akinesia. Results are illustrated in FIG. 15 show that the baclofen-acamprosate (3.75 mg/kg bid and 0.25 mg/kg bid, respectively) combination alleviates the lowering of double contacts on the cylinder induced by 6-OHDA intoxication, which shows an improvement of the rat spontaneous motor behavior.

Several doses and ratios of the drugs have been tested for the baclofen-acamprosate combination. Results gathered in table 8 below confirm that a large range of doses or ratios of baclofen and acamprosate are efficient in counteracting akinesia induced by the stereotaxic injection of 6-OHDA.

TABLE 8

| Baclofen-acamprosate (BCL-ACP) treatment | Protective effect against 6-OHDA induced akinesia* |
|---|---|
| dose 1: 0.6 mg/kg bid and 0.04 mg/kg bid | + |
| dose 2: 1.5 mg/kg bid and 0.1 mg/kg bid | + |
| dose 3: 3.75 mg/kg bid and 0.25 mg/kg bid | + |
| dose 4: 125 µg/kg bid and 2 µg/kg bid | + |
| dose 5: 125 µg/kg bid and 40 µg/kg bid | + |
| dose 6: 0.5 mg/kg bid and 8 µg/kg bid | + |
| dose 7: 0.5 mg/kg bid and 20 µg/kg bid | + |

*in at least one of ITT, CT or ST

2) Improvement of Akinesia In Vivo is Related to a Reduced Neuronal Loss in Treated Animals Tissue Preparation for Macrohistology All animals were killed by lethal injection of pentobarbital. The brains were quickly removed, then frozen in dry ice and stored at −80° C.

Striatum slices preparation: Coronal (10 µm thick) tissue sections at the level of striatum were cut at −20° C. with a cryostat (HM560). Three serial striatal sections per animal were then mounted on SuperFrost Plus glass slides (Fisher Scientific) and stored at −80° C. until histological analysis.

Subtantia nigra pars compacta (SN) slices preparation: slices are distributed in three sets of sections covering the whole SN (coordinates: −4.8, −5.3 and −5.8 mm AP from bregma). SN slices, after rinses, were immersed in 0.3% $H_2O_2$, pre-incubated for 30 min in PBS containing 5% BSA, and then incubated overnight in the same solution containing a monoclonal Anti-Tyrosine Hydroxylase antibody (TH, Sigma) at the dilution of 1/1000. Section are subsequently incubated for two hours with a dye labelled anti-mouse secondary antibody.

Labelling of Dopaminergic Terminals Neurons in Striatum with [$^3$H]-Mazindol Staining The loss of DA terminals in the striatum was assessed as an index of the extent of the dopaminergic denervation by analysis of [$^3$H]-mazindol binding to dopamine uptake sites [40]. Indeed, mazindol is a blocker of dopamine reuptake transporter which is commonly used to label dopaminergic neurons in experimental biology.

Briefly, striatal section were air dried (with a laboratory air dryer) and rinsed for 5 min in 50 mM Tris buffer with 120 mM NaCl and 5 mM KCl. They were then incubated for 40 min with 15 nM [$^3$H]-mazindol (NEN, DuPont; specific activity, 17 Ci/mM) in 50 mM Tris buffer containing 300 mM NaCl and 5 mM KCl added with 0.3 mM desipramine to block the noradrenalin uptake sites. Sections were rinsed twice for 3 min in the Tris incubation buffer and for 10 s in distilled water and were air dried. [$^3$H]-sensitive photographic fit (Kodal BioMax MS Film, Sigma) was exposed to the slices in x-ray cassettes and exposed at room temperature for 3 weeks. The levels of [$^3$H]-mazindol labelling was quantified by digitized image analysis from the film autoradiograms using as BIOCOM analysis system (Densirag, BIOCOM). Grey levels were converted to optical densities (ODs) using external standards (calibrated density step tablet, Kodak). The mean OD value was determined from three sections per animal after subtracting the background signal measured on each section by scanning an area of the corpus callosum that is known to lack DA terminals.

Quantification of TH Positive Neuron in SN

TH positive neurons were counted in a set of the three sections centered on the track of the 6-OHDA injection needle in the SN, covering almost all the SN. The specificity of DA neuron damage, global cells in the SN are counted on toluidine blue labelled sections of the same region. Cell counted is done using a microscope connected to a computer image analysis system by a CDD camera.

Results

Figure 16:
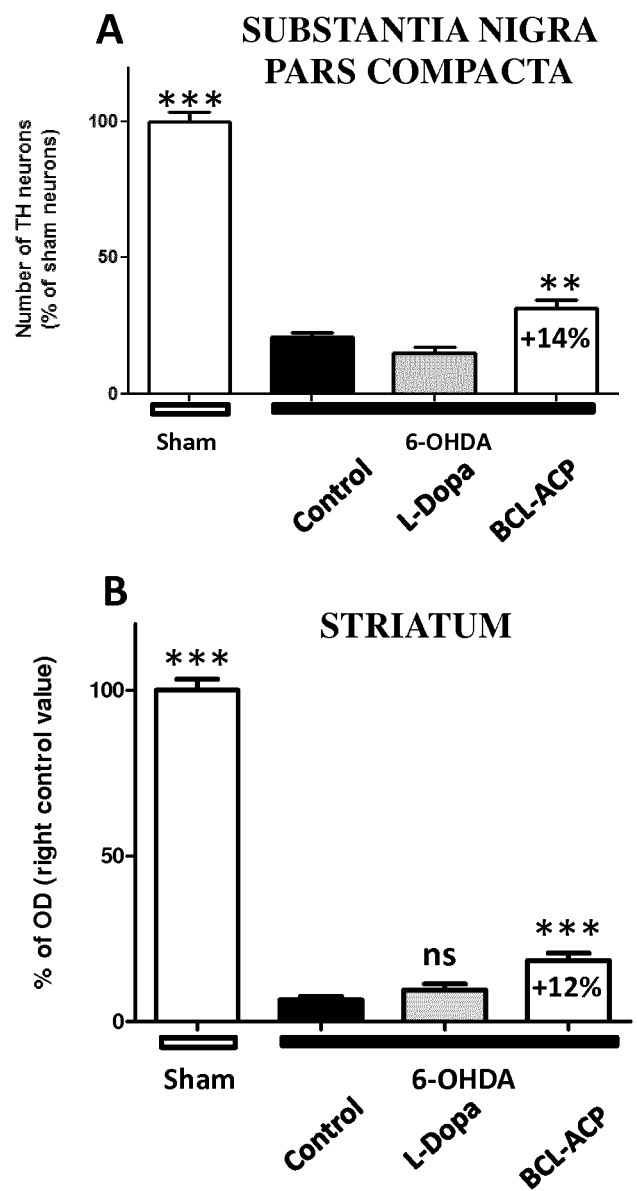
FIG. 16: Baclofen and acamprosate combination therapy (BCL-ACP; 3.75 mg/kg bid and 0.25 mg/kg bid, respectively) protects dopaminergic neurons from death in vivo. A: BCL-ACP protects dopaminergic neuron cell bodies of subtantia nigra pars compacta (SN) from the 6-OHDA stereotaxic lesion in the left SN. The number of dopaminergic neurons is found significantly increased in the left (intoxicated) part of SN of BCL-ACP treated rats when compared to the number of neurons in the left (intoxicated) part of SN of non-treated animals. Such a neuroprotective effect is not observed in L-DOPA treated rats. B: BCL-ACP protects striatal axonal projections of dopaminergic neurons after the 6-OHDA stereotaxic lesion in the left substantia nigra pars compacta (SN). BCL-ACP treatment significantly increased the density, in the left striatum, of dopaminergic neuronal terminals from the left part (6-OHDA intoxicated) of substantia nigra when compared to the left striatum of non-treated intoxicated rats (control, black bar). Such a neuroprotective effect is not observed for L-DOPA treated rats. OD: optical density related to the level of $H^3$-mazindol labelling of dopaminergic terminals in the striatum; labelling is expressed as the % of the OD obtained for the right part of striatum.*: $p<0.001$; : $p<0.01$: significantly different from control; ns: not significantly different from control (ANOVA+Dunett's test).

The 6-OHDA injection in the left SN results in the decrease of the density of both the DA cellular bodies in the SN and the DA terminals density in the left side of the striatum (FIG. 16). L-DOPA, which is recognized as an only symptomatic treatment of PD, failed to inhibit this 6-OHDA induced loss of neurons. Administration of dose 3 of baclofen-acamprosate combination (3.75 mg/kg bid and 0.25 mg/kg bid, respectively) induced a statistically significant elevation of DA neurons in the SN and also in the striatum when compared with non-treated animals (FIG. 16). Hence baclofen-acamprosate combination affords an actual protection of DA neurons against degeneration induced by 6-OHDA to the difference of L-DOPA, the currently most efficient treatment though only symptomatic. Not only cellular bodies of DA neurons of SN but also nerve terminals in the striatum are protected, hence this protection seems to act also against an anterograde neuronal degeneration.

REFERENCES

1 De Lau L M L & Breteler M M B (2006) Epidemiology of Parkinson's disease. *Lancet Neurol.* 5, 525-35.
2 Samii A, Nutt J G & Ransom B R (2004) Parkinson's disease. *Lancet* 363, 1783-93.
3 Savitt J M, Dawson V L & Dawson T M (2006) Diagnosis and treatment of Parkinson disease: molecules to medicine. *J. Clin. Invest.* 116, 1744-54.
4 Schapira A H & Jenner P (2011) Etiology and pathogenesis of Parkinson's disease. *Mov. Disord.* 26, 1049-55.
5 Gao H-M & Hong J-S (2011) Gene-environment interactions: key to unraveling the mystery of Parkinson's disease. *Prog. Neurobiol.* 94, 1-19.
6 Kahle P J, Waak J & Gasser T (2009) DJ-1 and prevention of oxidative stress in Parkinson's disease and other age-related disorders. *Free Radic. Biol. Med.* 47, 1354-61.
7 Lee D W, Rajagopalan S, Siddiq A, Gwiazda R, Yang L, Beal M F, Ratan R R & Andersen J K (2009) Inhibition of prolyl hydroxylase protects against 1-methyl-4-phenyl-1,2,3,6-tetrahydropyridine-induced neurotoxicity: model for the potential involvement of the hypoxia-inducible factor pathway in Parkinson disease. *J. Biol. Chem.* 284, 29065-76.
8 Abbott A (2010) Levodopa: the story so far. *Nature* 466, S6-7.
9 Rascol O, Lozano A, Stern M & Poewe W (2011) Milestones in Parkinson's disease therapeutics. *Mov. Disord.* 26, 1072-82.
10 Obeso J A, Rodriguez-Oroz M C, Goetz C G, Marin C, Kordower J H, Rodriguez M, Hirsch E C, Farrer M, Schapira A H V & Halliday G (2010) Missing pieces in the Parkinson's disease puzzle. *Nat. Med.* 16, 653-61.
11 Ettmayer P, Amidon G L, Clement B & Testa B (2004) Lessons learned from marketed and investigational prodrugs. *J. Med. Chem.* 47, 2393-404.
12 Beaumont K, Webster R, Gardner I & Dack K (2003) Design of ester prodrugs to enhance oral absorption of poorly permeable compounds: challenges to the discovery scientist. *Curr. Drug Metab.* 4, 461-85.
13 Heimbach T, Oh D M, Li L Y, Rodriguez-Hornedo N, Garcia G & Fleisher D (2003) Enzyme-mediated precipitation of parent drugs from their phosphate prodrugs. *Int. J. Pharm.* 261, 81-92.
14 Yang C Y, Dantzig A H & Pidgeon C (1999) Intestinal peptide transport systems and oral drug availability. *Pharm. Res.* 16, 1331-43.
15 Steffansen B, Nielsen C U, Brodin B, Eriksson A H, Andersen R & Frokjaer S (2004) Intestinal solute carriers: an overview of trends and strategies for improving oral drug absorption. *Eur. J. Pharm. Sci.* 21, 3-16.
16 Stella V J (2007) *Prodrugs: challenges and rewards*. (A. Press and Springer, eds.) Springer Singapore Pte. Limited, New-York.
17 Wermuth C G (2003) Designing prodrugs and biopre-cusrors. In *The Practice of Medicinal Chemistry* (Hardbound, ed), 2nd ed., pp. 561-585. Academic Press.
18 Pezron I, Mitra A K, Duvvuri S & Tirucherai G S (2002) Prodrug strategies in nasal drug delivery. *Expert Opin. Ther. Pat.* 12, 331-340.
19 Stella V J (2004) Prodrugs as therapeutics. *Expert Opin. Ther. Pat.* 14, 277-280.
20 Stella V J & Nti-Addae K W (2007) Prodrug strategies to overcome poor water solubility. *Adv. Drug Deliv. Rev.* 59, 677-94.
21 Higuchi T & Stella V J (1975) *Pro-drugs as Novel Drug Delivery System*, ACS Sympos American Chemical Society, Washington, D C.
22 Roche E B (1977) *Design of biopharmaceutical properties through prodrugs and analogs: a symposium*, American P The Academy, Washington, D C.
23 Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *J. Pharmacol. Exp. Ther.* 330, 911-21.
24 Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorg. Med. Chem. Lett.* 21, 6582-5.
25 Hanafi R, Mosad S, Abouzid K, Niess R & Spahn-Langguth H (2011) Baclofen ester and carbamate prodrug candidates: a simultaneous chromatographic assay, resolution optimized with DryLab. *J. Pharm. Biomed. Anal.* 56, 569-76.
26 Leach A R & Gillet V J *An Introduction to Chemoinformatics* (Springer-Verlag New York Inc, ed.).
27 Rahman S A, Bashton M, Holliday G L, Schrader R & Thornton J M (2009) Small Molecule Subgraph Detector (SMSD) toolkit. *J. Cheminform.* 1, 12.
28 Neugebauer G, Besenfelder E & von Mollendorff E (1988) Pharmacokinetics and metabolism of torasemide in man. *Arzneimittelforschung.* 38, 164-6.
29 Stahl H & Wermuth C G (2011) *Pharmaceutical salts: Properties, selection, and use,* 2nd ed. (Wiley-VCH, ed.).
30 Gennaro A R (2000) *Remington: The Science and Practice of Pharmacy,* 20th ed. (A. D. Gennaro, W. Lippincott, and Wilkins, eds.) Lippincott Williams & Wilkins.
31 Swarbrick J & Boylan J C (eds.) *Encyclopedia of Pharmaceutical Technology* Dekker, Marcel, New-York.
32 Slinker B K (1998) The Statistics of Synergism. *J. Mol. Cell. Cardiol.* 30, 723-731.

33 LOEWE S (1953) The problem of synergism and antagonism of combined drugs. *Arzneimittelforschung.* 3, 285-90.
34 Grabovsky Y & Tallarida R J (2004) Isobolographic analysis for combinations of a full and partial agonist: curved isoboles. *J. Pharmacol. Exp. Ther.* 310, 981-6.
35 Singer C A, Figueroa-Masot X A, Batchelor R H & Dorsa D M (1999) The mitogen-activated protein kinase pathway mediates estrogen neuroprotection after glutamate toxicity in primary cortical neurons. *J. Neurosci.* 19, 2455-63.
36 Schinelli S, Zuddas A, Kopin I J, Barker J L & di Porzio U (1988) 1-Methyl-4-phenyl-1,2,3,6-tetrahydropyridine metabolism and 1-methyl-4-phenylpyridinium uptake in dissociated cell cultures from the embryonic mesencephalon. *J. Neurochem.* 50, 1900-7.
37 De GROOT (1959) The rat hypothalamus in stereotaxic coordinates. *J. Comp. Neurol.* 113, 389-400.
38 Olsson M, Nikkhah G, Bentlage C & Bjorklund A (1995) Forelimb akinesia in the rat Parkinson model: differential effects of dopamine agonists and nigral transplants as assessed by a new stepping test. *J. Neurosci.* 15, 3863-75.
39 Lundblad M, Andersson M, Winkler C, Kirik D, Wierup N & Cenci M A (2002) Pharmacological validation of behavioural measures of akinesia and dyskinesia in a rat model of Parkinson's disease. *Eur. J. Neurosci.* 15, 120-32.
40 Jouve L, Salin P, Melon C & Kerkerian-Le Goff L (2010) Deep brain stimulation of the center median-parafascicular complex of the thalamus has efficient anti-parkinsonian action associated with widespread cellular responses in the basal ganglia network in a rat model of Parkinson's disease. *J. Neurosci.* 30, 9919-28.

The invention claimed is:

1. A method of treating Parkinson's disease in a subject in need thereof, comprising administering to said subject an effective amount of tadalafil and cinacalcet and, optionally, a dopamine precursor, a dopamine receptor agonist, an inhibitor of a dopamine metabolizing enzyme, baclofen, mexiletine, sulfisoxazole and torasemide, or salt(s), prodrug(s) or sustained release formulation(s) thereof as the sole active ingredients, wherein the subject has Parkinson's disease.

2. The method of claim 1, said method comprising administering to said subject a further compound selected from baclofen, mexiletine, sulfisoxazole and torasemide or salt(s), prodrug(s) or sustained release formulation(s) thereof.

3. The method of claim 2, comprising administering to said subject at least one of the following combinations of compounds:
tadalafil, cinacalcet and mexiletine, or
tadalafil, cinacalcet and baclofen,
or salt(s), prodrug(s) or sustained release formulation(s) thereof.

4. The method of claim 1, comprising further administering to said subject at least one of: a dopamine precursor, a dopamine receptor agonist, or an inhibitor of a dopamine metabolizing enzyme.

5. The method of claim 4, wherein the dopamine precursor is levodopa or melevodopa or salts, prodrugs or sustained release formulation thereof; the dopamine receptor agonist is a compound selected from the group consisting of talipexole, piribedil, rotigotine, bromocriptine, pergolide, cabergoline, lisuride, pramipexole, ropinirole or apomorphine or salts, prodrugs or sustained release formulations thereof; and the inhibitor of a dopamine metabolizing enzyme is a compound selected from the group consisting of carbidopa, benserazide, entacapone, tolcapone, selegiline and rasagiline, or salt(s), prodrug(s) or sustained release formulations thereof.

6. The method of claim 5, comprising administering to said subject at least one of the following combinations of compounds:
tadalafil, cinacalcet and levodopa,
tadalafil, cinacalcet, mexiletine and levodopa, or
tadalafil, cinacalcet, baclofen and levodopa,
or salt(s), prodrug(s) or sustained release formulation(s) thereof.

7. The method of claim 6, further comprising administering to said subject at least one compound selected from carbidopa, benserazide, entacapone, tolcapone, selegiline and rasagiline, or a salt, prodrug or sustained release formulation thereof.

8. The method of claim 7, wherein said at least one compound is carbidopa, or a salt, prodrug or sustained release formulation thereof.

9. The method of claim 5, comprising administering to said subject at least one of the following combinations of compounds:
tadalafil, cinacalcet and selegiline or rasagiline,
tadalafil, cinacalcet, mexiletine and selegiline or rasagiline, or
tadalafil, cinacalcet, baclofen and selegiline or rasagiline,
or salt(s), prodrug(s) or sustained release formulation(s) thereof.

10. The method of claim 1, wherein the compounds are administered with a pharmaceutically acceptable carrier or excipient.

11. The method of claim 1, wherein the compounds are formulated or administered together, separately or sequentially.

12. The method of claim 1, wherein the compounds are administered repeatedly to the subject.

13. The method of claim 1, wherein the compounds are administered orally.

14. The method of claim 1, wherein said administration protects dopaminergic neurons of the nigrostriatal system of the subject from degeneration or death.

15. The method of claim 1, wherein said administration treats bradykinesia or akinesia in said subject.

16. The method of claim 1, wherein said subject is also treated with deep brain stimulation of the subthalamic nucleus or of the globus pallidus interna.

17. The method of claim 1, said method comprising administering tadalafil and cinacalcet or salt(s), prodrug(s) or sustained release formulation(s) thereof as the sole active ingredients.

18. A composition comprising tadalafil and cinacalcet and, optionally, a dopamine precursor, a dopamine receptor agonist, an inhibitor of a dopamine metabolizing enzyme, baclofen, mexiletine, sulfisoxazole and torasemide, or salt(s), prodrug(s) or sustained release formulation(s) thereof.

19. The composition of claim 18, said composition further comprising a compound selected from baclofen, mexiletine, sulfisoxazole and torasemide or salt(s), prodrug(s) or sustained release formulation(s) thereof.

20. The composition of claim 19, said composition comprising:
tadalafil, cinacalcet and mexiletine,
or
tadalafil, cinacalcet and baclofen,
or salt(s), prodrug(s), or sustained release formulation(s) thereof.

21. The composition of claim 20, said composition further comprising a dopamine precursor selected from levodopa or melevodopa or salts, prodrugs or sustained release formulation thereof.

22. The composition of claim 20, said composition further comprising an inhibitor of a dopamine metabolizing enzyme selected from selegiline or rasagiline, or any pharmaceutically acceptable salt(s), prodrug(s), or sustained release formulation thereof.

23. The composition of claim 20, said composition further comprising an inhibitor of a dopamine metabolizing enzyme selected from carbidopa, benserazide, entacapone, tolcapone, selegiline and rasagiline, or any pharmaceutically acceptable salt(s), prodrug(s), or sustained release formulation thereof.

24. The composition of claim 18, said composition further comprising a dopamine receptor agonist selected from the group consisting of talipexole, piribedil, rotigotine, bromocriptine, pergolide, cabergoline, lisuride, pramipexole, ropinirole and apomorphine or salts, prodrugs or sustained release formulations thereof.

* * * * *

UNITED STATES PATENT AND TRADEMARK OFFICE
CERTIFICATE OF CORRECTION

PATENT NO. : 10,342,768 B2
APPLICATION NO. : 15/506308
DATED : July 9, 2019
INVENTOR(S) : Daniel Cohen et al.

Page 1 of 1

It is certified that error appears in the above-identified patent and that said Letters Patent is hereby corrected as shown below:

In the Specification

Column 6,
Line 1, "0: <0.05:" should read --◊: <0.05:--.

Signed and Sealed this
Sixteenth Day of June, 2020

Andrei Iancu
*Director of the United States Patent and Trademark Office*